US008808996B2

(12) United States Patent
Schuren et al.

(10) Patent No.: US 8,808,996 B2
(45) Date of Patent: Aug. 19, 2014

(54) **MARKERS FOR DETECTION OF *LEGIONELLA PNEUMOPHILA* STRAINS**

(75) Inventors: Frank Henri Johan Schuren, Veenendaal (NL); Waatze Aize Atsma, Leeuwarden (NL)

(73) Assignees: Nederlandse Organisatie voor Toegepast-Natuurwetenschappelijk Onderzoek TNO, Delft (NL); Vitens N.V., Utrecht (NL)

( * ) Notice: Subject to any disclaimer, the term of this patent is extended or adjusted under 35 U.S.C. 154(b) by 596 days.

(21) Appl. No.: 13/001,389

(22) PCT Filed: Jul. 1, 2009

(86) PCT No.: PCT/NL2009/050391
§ 371 (c)(1),
(2), (4) Date: Apr. 6, 2011

(87) PCT Pub. No.: WO2010/002254
PCT Pub. Date: Jan. 7, 2010

(65) Prior Publication Data

US 2011/0207127 A1 Aug. 25, 2011

(30) Foreign Application Priority Data

Jul. 1, 2008 (EP) .................................... 08159457

(51) Int. Cl.
*C12Q 1/68* (2006.01)
*C12M 1/34* (2006.01)
*C07H 21/04* (2006.01)

(52) U.S. Cl.
USPC .................... 435/6.15; 435/287.2; 536/24.32

(58) Field of Classification Search
None
See application file for complete search history.

(56) References Cited

FOREIGN PATENT DOCUMENTS

WO WO-2005/049642 6/2005
WO WO-2008/082290 7/2008

OTHER PUBLICATIONS

Alignment of SEQ ID No. 1 with SEQ ID No. 6733 of WO2005049642A2 (no date); 5 pages.*

International Search Report for PCT/NL2009/050391, mailed Oct. 6, 2009, 4 pages.

International Preliminary Report on Patentability for PCT/NL2009/050391, issued Jan. 5, 2011, 12 pages.

Database EBI XP002544187, Accession No. Q5WYD8_LEGPL, Nov. 1, 2004.

Cazalet et al., "Evidence in the *Legionella pneumophila* Genome for Exploitation of Host Cell Functions and High Genome Plasticity," Nature Genetics (2004) 36(11):1165-1173.

Gaia et al., "Sequence-Based Typing of *Legionella pneumophila* Serogroup 1 Offers the Potential for True Portability in Legionellosis Outbreak Investigation," Journal of Clinical Microbiology (2003) 41(7):2932-2939.

Database EBI XP002509567, Accession No. AEB39158, Sep. 8, 2005.

Database EBI XP002509568, Accession No. AEB39167, Sep. 8, 2005.

Database EBI XP002509569, Accession No. AEB35715, Sep. 8, 2005.

Database EBI XP002509570, Accession No. AEB39175, Sep. 8, 2005.

Database EBI XP002509571, Accession No. AEB35717, Sep. 8, 2005.

Database EBI XP002509572, Accession No. AEB42401, Sep. 8, 2005.

Database EBI XP002509573, Accession No. AEB39172, Sep. 8, 2005.

Database EBI XP002509574, Accession No. AEB42739, Sep. 8, 2005.

Database EBI XP002509575, Accession No. AEB35722, Sep. 8, 2005.

Database EBI XP002544185, Accession No. AEB35710, Sep. 8, 2005.

Database EBI XP002544186, Accession No. AEB38585, Sep. 8, 2005.

Database EBI XP002509576, Accession No. BZ557975, Dec. 23, 2002.

Database EBI XP002509577, Accession No. EJ328577, Mar. 12, 2007.

* cited by examiner

*Primary Examiner* — Diana B Johannsen
(74) *Attorney, Agent, or Firm* — Morrison & Foerster LLP

(57) ABSTRACT

The invention relates to a method of detecting *Legionella pneumophila* strains by hybridizing genomic DNA of a sample suspected to contain *Legionella* to one or morespecific sequence markers, as identified by SEQ ID NO:1 through SEQ ID NO:10 or homologues thereof or in an immunoassay with antibodies specifically recognizing the amino acid sequence of SEQ ID NO: 11 and/or 12. The invention further relates to a kit of parts comprising an array and reference materials for performing a method of the invention.

7 Claims, No Drawings

SEQUENCE LISTING

```
<160> NUMBER OF SEQ ID NOS: 12

<210> SEQ ID NO 1
<211> LENGTH: 965
<212> TYPE: DNA
<213> ORGANISM: Legionella pneumophila
```

-continued

<400> SEQUENCE: 1

```
gaattcgtcg gaaaccaatc ggcggttttt tttaagccct cacatgaatc aacgggtgga      60
gtccagccta agtctgaaat aatctttgaa ctatcaattt ccagagaact cagcaagcga     120
gtatttaaac tgcccattcc tgtgatcttg aacaggccgg ctaaaaaagt agtagggaag     180
tgatacaatc ttaaattgat tttcatattt tgggctagta aggataacaa atccgctaaa     240
gaccaagatt cattatctgc tacaagataa agttgatttg ctgctttagg atgtgtcatt     300
accattagaa tagctgaaac caagttatca ataaaaataa aacttctctt attctttata     360
ctggcaaaag gcaatggcca tcctttttgt accataccca ataattttaa aaaattggct     420
tttactccag gtccataaac aagtggaggc ctcaagataa ccacttccat gtcactattt     480
tcactaatct cacgcaaata gagttccgct tctaacttac tctgagcata agaatctttt     540
ggttgggctg aatttttctc agaaaatggg ctctgaggta agcttacttc tccatttacc     600
ttaatagtac ttaaaaatac aaatcgcttt actttgtgtt ttgcagcttg ttgagcaaaa     660
ttcttggtgg cgatgctgtt tattttgcaa tactcttcca gagaggagga ggtatcctct     720
ctcataacat ggactcgcgc agccagatgt atgacaatat cgattccatt caaagcttct     780
gacccatccg ttacttgctc cagcttatca atttcaactt gctcaacaga catgtattga     840
tttttttgcc acacagcaca acgaacctca taccctgcag caataagaac cgggaaccaa     900
gctactgccc ataaaacctg gtgcgcccgt cactaatact tttgtcacta tattacctat     960
ggctt                                                                 965
```

<210> SEQ ID NO 2
<211> LENGTH: 1017
<212> TYPE: DNA
<213> ORGANISM: Legionella pneumophila

<400> SEQUENCE: 2

```
tgacgaatca gagattcgtc ttattaacct ttttctatgg aaaaacgcat ggtgggacaa      60
agtattctgc tgaacatcac ctaaatgaat ataaaaagaa tctggaagat gatataaagg     120
caatcggtgt tcaaagaaaa atttcaccaa atgcctatga agatctatta aaagagaaaa     180
aagagcgcct ggaacaaatc gaaaaatata ttgatttaat caaagtactc aaagagaaat     240
ttgatgagca aagagaaata gacaaactac gcacagaagg aatcccgcaa ttaccttctg     300
gagtaaagga agtcattaaa tcttctgaaa atgcctttgc tttaaggctt tccccggata     360
gaccagactc atttacccgc tttgatgatc ctctgtttag tctcaaaaga aacagatctc     420
aatatgaagc tgggggatac caacgggcaa ctgatggatt aggggctcgt ttgcgttctg     480
agcttctacc accagataaa gacactccta ttgtttttaa taaaaaatca ctgaaggaca     540
aaatcgtaga ttctgtttta gtgcaacttg acaaagattt taataccaaa gatggcgatc     600
gtggtcaaaa atttgaggat ataaaaaaac tcgttctaga agagtacaag aaaattgatt     660
ccgaccttca ggtggatgag gatacctatc accaacccct taacttggat tatttggaaa     720
acatagcatg tacgttagat gaacactccc ctcgcaaaga atgagtttat ggaattatgg     780
gtgcccccaa ccgaagctga ttatgggccc aaaaaaggaa agggcaacgt ggaactgaac     840
aacttagtgg tatttattaa caaccccaag gaatataaaa tttgaatctg aatacaaata     900
ccatggccac ttacggtcca atattcaata actgaagatt attttttatt ggcaaacccc     960
accaccttct caaagtccaa atttcggtga attttttgca ataaacaccc cccaggc       1017
```

<210> SEQ ID NO 3
<211> LENGTH: 1495
<212> TYPE: DNA
<213> ORGANISM: Legionella pneumophila
<220> FEATURE:
<221> NAME/KEY: misc_feature
<222> LOCATION: (776)..(776)
<223> OTHER INFORMATION: n is a, c, g, or t

<400> SEQUENCE: 3

```
cgcgaaccga gaaccgttcg gaggcgatga gaacggaacc gataacactc gtccaaacag     60

cagttgaatt aagatcattc ccctacggaa atactccacc acggcgaagc taggcattcc    120

cgctgagcaa cagctcgact cgattataaa aaacaactcg gaagaagaca taaaagccat    180

caatagccaa aaagggatat cacgttcatc gcttataccg attctcgtta agggaaaaaa    240

aggaacgact taaacaaatt cgaaaaatac attcgagtta attcaacgta ctcaaaacag    300

aatatgatca caacggtgaa ataatgacta taaaaaataa cattattcca cctctacctt    360

tccggattaa accaaataat ccagtcttct gagaatgctg gtgctgtaag actgtcccca    420

gatcgccctg atttggcaac cagttttaaa aacccttat tcaggttaaa tagacattat    480

gaaaccagcg attataaact gacagaaggc ttaggggttc gcctcagttc aacgctcttg    540

ccagatcctg aaactcctac gccaattaat agaaaatcac aaaaagaaaa aattgtagaa    600

actgttttag ctaaatttca accagaaaaa atagctgaac cagaccgtga ccaaaaattg    660

aaagagctaa aagccctttc ttcagaagag cttgtaaaaa ttgactccaa tttgtcagtg    720

gatataagcc atgataaaca agagacaaac tacgactatc tggaaaatat gatggncatg    780

gatgaagata gtttcatcag gaatggggtt tgatctattc tcacagcgac agtagattcg    840

agcgcttggg gttactcaat cccgcagtcc tttctatgat ggcgccaaag aataaacaaa    900

aagacgatgc ggataaaatg tccatcaaag tacaatacct aatagccgag gctaattttt    960

attgtaaaac gaacaaatat tccatgctaa ctttcgggaa attttttga caaggagcct   1020

catgccactg aaattgcgaa aagagtcaaa gaaggattgg tgcaaggagt agatatagag   1080

cctatcatat acaattacat caacagcaac catgcagagc ttggattaaa atcccctttg   1140

actgccaaac aacaacaaga aatcaccgat aaattttcgc aacattacaa taccattaag   1200

gactcccctc attttgatga attttttatc gctgatcctg ataagaaggg aaatatattt   1260

acccatcagg gcagactcag ttgccatttc cttgacttct ttgcccgaca aactaacgcc   1320

aaacatcttt tgggagaact tgacggtcac gcagaagcat tactggaagg aacttcaaat   1380

cgcttaaatc ataaaaatga aattgtggcg gaaggatatg agaaaataga gcaatttaac   1440

aagaagtagt aaggcttctg gctgaaaata acccaaagaa tgaacgattc agctg         1495
```

<210> SEQ ID NO 4
<211> LENGTH: 1407
<212> TYPE: DNA
<213> ORGANISM: Legionella pneumophila
<220> FEATURE:
<221> NAME/KEY: misc_feature
<222> LOCATION: (634)..(634)
<223> OTHER INFORMATION: n is a, c, g, or t

<400> SEQUENCE: 4

```
gaatcgtctc gatctggtag cctcaaggat tctgacattg cctccttcgc cagcgcgtcg     60

cacgaataca agggctgctc gtcattaacc ccaaacggtg ccgtcgtgat cgttatcacc    120

cggtcgccat tccttacacc aacgacggag gatcgtgctt ttccagtcgt tttgcgtgag    180
```

-continued

```
ccagtctttg cgcaaaaaaa ccagattttc caagatttgc taaccgtagt gaagcaacga    240
gatgatgaaa agttgctgga gcgagtgttt gttctggttc gttatggttg tatatatacc    300
ggcacattac gtgtaaataa cattccagct ggtccatgga aacatttttt ctatgttcaa    360
acagttaaca tcgcaacaag tgatatgaag ccgctgctgg cagcgcaaat tattggcggc    420
ttacctgttt cccaaaatgc taaagcggac ctggatatag cctgtggacc actcacttgg    480
gaagatggtg agtttgatat tgagttgata tagagtgtac tgcagggctg attcatattg    540
gctaatagcc atggaataat gtgagttgta ttgataagta ataccttaac tctgtacggt    600
acgatttttg ggaccgtcgt tgcgaggagc gtancgacga agcaatccag tggcctgaat    660
tcgttgaagt agctcactga ttcattgata acccatattt tttccgctaa gaaacgacat    720
ggagtcgtga atgagtatca ctgagctggc agatatttta aatggttatt tttcatggaa    780
caagtcgcga atcgagtgtt ttgcgacgat gttaatctct ttaattcaag taagaaaggt    840
caatttaact gaaattgcat gtgggttttc tagccctgct aaaaaagatt caaggtacac    900
aagaatcaaa ccattttgaa aaaccacgca tgactcaacc ggatcgcatt gaaaaactac    960
tggtgctatt gaacattgct tttgttgggg cccctaaaaa tggagagtgg cggcatgttc   1020
agaagacaat taaaatcaaa aaacatggtc gcaaaggggt aagttttttt cgttatggac   1080
ttgatttatt acatgatgct gcgcttaatg gctgtcagtt tattcaccat tctttctccg   1140
atatacttgg gtttttgtgc attagtcgcg tgatatgcgc tgctgaatga attggtccaa   1200
taacaaggaa gaagcatgca agtgaaacaa ccagccattt acatcatggc gaataaacgc   1260
aatggaacga tctacacggg tgtcacaagc gatttgatca aacgtgtcta tgaacataaa   1320
tatggggatg tacccgggtt tactcaagag catggatgta agtttcttgt tactatgagc   1380
tcatgaagac agaacgaatc aagctgt                                       1407
```

<210> SEQ ID NO 5
<211> LENGTH: 1153
<212> TYPE: DNA
<213> ORGANISM: Legionella pneumophila

<400> SEQUENCE: 5

```
agctgattcg tttttagttg tttttctcga gctatggcac ttatcatgtc ttcaatgagc     60
tcatagtaaa caagaaactt acatccatgc tcttgagtaa acccgggtac atccccatat    120
ttatgttcaa tagacacgtt tgatcaaatc gcttgtgaca cccgtgtaga ttgttccatt    180
gcgtttattc gccatgatgt aaatggctgg ttgtttcact tgcatgcttc ttccttgtta    240
ttggaccaat tcattcagca gcgcatatca cgcgactaat gcacaaaaac ccaagtatat    300
cggagaaaga atggtgaata aactgacagc cattaagcgc agcatcacgt aataaatcaa    360
gtccataacg aaaaaaactt accccttttgc gaccatgttt tttgatttta attgccttct    420
gaacatgccg ccactctcca gttttatggg cccaacaaaa agcaatggtc aatagcacca    480
gtaatttttc aatgcgatcg gttgagtcat gtgtgtgtct tcaaaatcgt ttgattcttg    540
tgtaccttga atcttgttta gcagggctag aaaaaccaca tgcaatctca gttaaattga    600
ccgttcttac tttgattaaa gagattaaca tcgtcgcaaa acactcgatt cgcgacttgt    660
tccatgaaaa ataaccattt aaaatatctg ccagatcagt gatactcatt cacgactcca    720
tgtcgtttct tagcggaaaa aatatggatt atcaatgaat cagtgagcta cttcaacgaa    780
ttcaggccac tggaatggct tcgtcgctac gctcctcgca acgacggtcc caaaaatcgt    840
accgtacaga gctacaaaac agacaaggat aatcaggaag ccttttttatt ttgtcgcttt    900
```

-continued

```
gctacctcaa gaaatgtata ctggcattct gtaacattac caaccatgtc atttgtcatg     960

acggggtgtc gctaaaactt gagacatgta aagtattaaa atactataag gcgaagaagc    1020

agattaaatc gaaaggggaa tttcagtaaa ccgaatgcca ccgaaaagga tcctaaataa    1080

ggaaataata gagatggatc ccgtgtacat gataaaccac accagaggcg agcctttctc    1140

gaagaaagac gat                                                       1153
```

```
<210> SEQ ID NO 6
<211> LENGTH: 1412
<212> TYPE: DNA
<213> ORGANISM: Legionella pneumophila

<400> SEQUENCE: 6

aatcagctga ttcgttatgg gtttatagtc catcttgaat catgtacaaa cgagaaattg      60

accttgaaaa taaggcaata aaagtcctga ctgaggaaga taacaaaagc tatgaaaaac     120

aggtcaaagc gcaattagat aatattaaaa atgttttaga atcacttgaa atgaaaataa     180

ttagccattc tgaacaatgg gagaaaatta gaaatcccgc aattcaaaaa gcgaaagaat     240

actatttagg tgacatggaa aaaggtaact gggtaactca atgggtaacg cagtcctgga     300

ttaatgagct atcctctctt cattccacca gtgaatttat ttatgagtta aatgctttac     360

ccccaagaaa aagagtacgt tttattgaag gtgaagaaca aagtgttgat accaccttgg     420

aaaatttaag aaatcaaatt attgatcgct gtggtttgcg aagcatgatt gatgcggaag     480

acaactctcc tgaacaacaa ttattgaaaa aatcaattga atactatgcc cactcgctgg     540

ccatttcaat gcagcgctcc tttttagtta agattcctgg aactaataat tatcaggaat     600

ttgacggcat caatgacaaa ggggagataa tagaacgcaa agaaaacaat ggaacaggca     660

aagattattt gcaaagtaat tttacccaaa gaaaaattaa cgagaaaatg aagtttttca     720

gggcagtcaa agcgtatcac ctccatttga tgtccgaatt acctgaaaat ccagaacaat     780

ataaaaacag ctatatattt atcaaaaata acgatactaa ggagctgtat tatataaaac     840

ctgatgggaa atatgaaaaa gtaaaaatta tcaaattcga tttaattgaa gaaaaaatag     900

ataacaataa agatgcgaat aaattaatcc ttctcagtaa ggaagaaatt aaagaaattg     960

taacattaaa cggaggccac tccccagcag aagagcacca tactaaattc actgttaacg    1020

atgtggcttt aaaactaatg ggaggcaaac ctgcctatcc gtttgctcga aaatggtttg    1080

gtcctaaatt tgatgaagcc ttgaaacatc gaatgaacgt tgctgccaaa tccctgctcg    1140

ttgatgcaat aaatcatccc aaaattcact ttgtatttaa ccgttcacat ggaacgaatt    1200

gaagattctc tgcgaagaaa ttattataat tctgacttaa ttaaaaaggt cgagtttaaa    1260

cgagtctacg cgagatgcgg gcgaatgaat acgcgcttgt aagaagaacg aatttgaagc    1320

ccacactttt ttccataatc gatgcggaaa aacaacttac ggaacgtggc gttactattc    1380

cagagtttcc gatgaagact ttacgacggt tc                                  1412
```

```
<210> SEQ ID NO 7
<211> LENGTH: 1469
<212> TYPE: DNA
<213> ORGANISM: Legionella pneumophila

<400> SEQUENCE: 7

cgaatcagag attcgtcatg ggcatgccca ccagatggac tttatgaaag ttatgatttc      60

aaaatttatt ttaccgaccc ccaacgaaaa gccttcctta ttcaaatcga caatgaactg     120

gccggttttg ctttattaaa taaattcgga atccaagccg ttgattggag tataggggag     180
```

```
tttttcatcc tggctaaatt ccaagggaaa ggcattggtc aatcagtagc tcatcaacta    240

tggcgcactc atccaggtga atgggaaata tcggtcattc cggaaaacat accggcttta    300

tcgttttggc gccaggctgt aatgacctat actcttgaac ggtacaaaga acagataaag    360

acagtgaatt atgatatcca ccaaacccaa cgcattattt taagttttaa tacacaaaaa    420

cagaacaaat cttgtcattc cattccaaaa aaacctatta caatagattt cgtggataat    480

atccccaaat ctctggaaaa aaagatgaca gaagatctga tagcctatga aagaactcat    540

ggtattgatg tgaactacaa gcgtttttcg atagtactat ctgaaggagg ggtgacttgt    600

ggcgttatta atgcctttac tgcttttgcg gaaatataca tcgatgacat atgggtagat    660

aaagcatatc gtggtaaagg atatggcaga aaattactgc aaactcttga gaatcatttt    720

aaagggcaag gatttaataa tatcaattta tgtaccagcg cctttcaagc accggaattt    780

tacagaaaat gcggatatac ggctgaattt acacgaatca atcaagccaa tcccaagctt    840

tctaaaacct tctttgtgaa attttttgat gatgaaaatc aaacacaagg actattttga    900

aaaacagaac ttctaaataa cccccacatc ttattgatat tcagaagttc tgaaaaagta    960

attttcaatt aaagagacta attaaagtgc ctataaaccg tcttattcca actgattaca   1020

ttagtttgtt ttaagagaaa aatcctggga agtcagaaac caacgtcgaa tatttttttc   1080

ggagtattta tgatactggc accaatctct aataatagag gaatctatat cttccgggat   1140

gtcatgtatg cctcgagaaa aatttccctg taaaagcaat aaacctccca gattatgcaa   1200

ataaaactca gggtctataa aaatcattga agtaggatca tataagcaaa aattaatagg   1260

tttttatcg tataatacat cctgagcgtt gaaattgggg ccaaactcat catgaagccc   1320

taaattcccc aggattttgc catcaaacca ggctctggga tatttgctca tgatattttt   1380

accaccagtt gcagttaaaa taatatctgc tttagccact gctttttcaa gcttatcgcg   1440

atcctcggga gaatacgaat cagctgatt                                     1469


<210> SEQ ID NO 8
<211> LENGTH: 1253
<212> TYPE: DNA
<213> ORGANISM: Legionella pneumophila

<400> SEQUENCE: 8

aatctttatt agagaactct tctgggtctt aaggcatgaa tcatggggtt gtggagagaa     60

caatccattg aggcatttta ggcttatggt aaaaatgcaa atgccttaat gtattcgggt    120

caattatatt attgttgatt tgcaaaaccc agataacaca agattgggta gagttcgctg    180

acaaagccac aaaatttgcc tggcagtttg gtattggaag cctctatgcc ctcagtgact    240

cgttgttaat cgatatcaat tataatttta tttcaattgg cgaagtgagg aattcaggtc    300

agtataatgc tattgcagcc aataatactc cagcttcagg tgcgccaaca aaattcacca    360

acgtgtatag caaccaggct gaaattggta ttcattacca atttaatact tagcgccaat    420

tcaaggcagg ttgaagtaaa aagatgacat caatgggagc cactgtttaa cctgcccatt    480

gctatctact cggctgaaat gaaaactacc ttcgtactca ggtctttcct ggtttttagc    540

tgcctggtac ttcactcata gttttcctgg caaattttcc cgtaatttta cggactttac    600

ctcatgatgg aaaaagtggg cagtcaatct tccatgatgt taaacgagcg gtgctttaag    660

tagattgtaa tgtatataaa tcgttgtcct tgattgcgtt tcgctacatc atagctataa    720

ggttaataaa tattccaaat aaattgggaa gttggcttaa atgtgtctat atttgttagt    780

atgtgaacac ttccagaata tccaaactct acagtaggaa taaattgaat tgattttaga    840
```

| | |
|---|---|
| gtaagaaaat ggattgataa acagatttga atgtttcttg ttagcatctc aatcaagaca | 900 |
| aacaaggaaa gcataatgtc taagactata tattttttca gtaacaattt gaaactggaa | 960 |
| ggaaaactgg aagaaccaac aggtcaatgc cttggttatg ttttatttgc tcattgtttt | 1020 |
| acctgcggaa aagatatagc tgctgcaagc agaattgcca gcgctttggt tgctaatgga | 1080 |
| tttgcggtgt tacggtttga ttttactggc ttaggtagca gcgaaggttc cttttcagaa | 1140 |
| acgaattttt cttcaaatgt tgaagattta gttgctgccg ctgactattt aaggactcat | 1200 |
| tatcaagcac ctgttctttt gataggccat agtctgacga ttctctgatt cgt | 1253 |

<210> SEQ ID NO 9
<211> LENGTH: 1216
<212> TYPE: DNA
<213> ORGANISM: Legionella pneumophila
<220> FEATURE:
<221> NAME/KEY: misc_feature
<222> LOCATION: (704)..(704)
<223> OTHER INFORMATION: n is a, c, g, or t
<400> SEQUENCE: 9
agggtcagat cttgctcttc gcctttatcc ataaaagacg gcaagcttgg aattaacgct 60
tgataattat ttccccaacg cattccatta tctttcaaaa ggaattaact aagtccagga 120
gcagcgattg gtaagacttt tcgcgcatcg agttttctgg tgggctctat cacatcaaca 180
gtcgagggaa tagaaaagaa gcgatctatt tatcagatgc agacagagag aattttttat 240
ctgttttggg tgatgtttgt ttaaaatatc agtggttatg ccattcgtat tgtctgatga 300
caaatcatta ccatttactt attgaaactc cgctcggtaa cctttcaaaa ggaatgcgct 360
atctgaacgg ggtatacact cagaaattta ataaatcaca caagcgtatt gggcacgtcc 420
tgcaaggttg ctataaatct atattggtca ctactcaaga atttgcagaa ttataagaca 480
acattatatg caggaggcaa aggacaagat ctgacctacg ctctaaacta taataatagt 540
tatagataat tgactattgg gatattttta catgaattac ctattgctga ttatcctggg 600
atttgtaact gctcttggtt ttgctgcgaa tacaccttgt tctggaaaaa agggaggtat 660
ttctcattgt ttaggtgaat atttcgtatg taaagatggc tcantaagcc aatcaaaaaa 720
caaatgcatt gatctagata aaaaaaatgg tcaataaatt tcactcaatt ttgcttttta 780
tttcccttct ttttagttgc actgcctatg caaataccat tagcggattg gttataaaaa 840
tatcagatgg tgatacatta actatcctca ctaaggataa cgttcaactt aaaattcgtt 900
tatcagaaat tgatgcacca gagaaaaaac aaccatttgg aaataaatcc aagcagtcgc 960
tctcaaatct ttgttttaat aaagtagcga tagttgatat tttaaaaatt gatagatatg 1020
gccgctctgt tggcagagtt aaatgtgata atgttgatgc taatgaatac caagtaaaaa 1080
atgggcttgc atgggtgtat gataaatatg ttacagatca ttcgttatat gcgcttcagg 1140
aacaagctaa aagcaaggga ataggtttgt ggtcggaaaa atcccccatc cctcctggat 1200
ttcagacaaa ttagcc 1216

<210> SEQ ID NO 10
<211> LENGTH: 1710
<212> TYPE: DNA
<213> ORGANISM: Legionella pneumophila
<400> SEQUENCE: 10
aaaggagact tggcagctct caagaacttg tttggttgca agcaaaaact tcaacccggc 60
tctctaatta gccttgataa tacaaccttt gcctttcctt gtaagggagt tcctacccaa 120

-continued

```
tactgggatc tggtaaatgg ctgggaatta caaaacaagg tatctatagg tgaacccatt    180

aaatggtcgg atattaagca aaaaaatgat tgttaaaaac cctacttgga actctcttac    240

ccctccactt cctaaatttg tttcttgtga tacaggcgag acaaatttcc tgaaagaaaa    300

attaggagaa gatgggaggg tttttattgc tcaatttgat ctaaaatcca cctctgcttt    360

tttatttcag cgtaaaagtg atcaaaaaaa attttttatc aagaaagtat ccgctgaaca    420

taaaagacag tatcagcaga gcgaacattt ggctcaattt atcgcttgcc cagattatat    480

agttaatatt gcaattaact gcgtttctaa tgaagaagaa aactcactct attatattta    540

tccctatatt catggaaaac gcctctttgc tgaaccagag gaaataataa gccttgcaac    600

tgcattagca aaattacatc ttaaaaaaaa atcttatcct gatcaacaat tgattattaa    660

aaatactacg gaacgaacat cacagcttaa ttttataaga aaggctttag ctaatggatg    720

ttattcctac attccatatt tctcttttgt taaaaagatg gctcaacaat atgattttga    780

ttggattaat caagaagatg cccaaccaat tcatggtgat ttaaatgcag gaaatctgtt    840

actatccgaa aataatatga tttgcttttt tgactttgaa gacgcattac atagtttcca    900

tccagtagta ttagatttgc tattcgtcat tgagcgtatt atttttaatc aaaatagttc    960

gactgaacgg ctattaaacc ttggtctcat gtttattcat gcatataaaa aggctggtgg   1020

tacataccgg tataaaacga gagatgaatt tggattaaca attcttgctt taaaagcatt   1080

ttgcttgttg actttgctag cagagaaaaa taaaaatata ctgaactcgg aatgggataa   1140

attttttaaa ttaactcaga aagcagaaaa tgaacgggat ttaataaaaa caattttaca   1200

aggataagaa agatagtgtg agagttcttg ttactgcacg ggatgttggt gctgcattaa   1260

acattattga gatagtaaaa atacttaaac aatatacagg tgttactgta tatatttatg   1320

ctcaacctcc cgcttcaaaa tattttcttc gggctgggat tcaatctgta tttcaagttc   1380

cactaccacc aacccgatcc tcaaatgaat ccaatcatct actatcctac gccaatcaat   1440

taattgataa attaaatccc gatatcatat tatctggatt atcatctcct ggcgaagctg   1500

gcatagatga agcaataata gctgtgtgtc ccgcgcatat caaaacattc atccttcaag   1560

atttttgggg agaagttaat tttttctttg aaaaattagc ggattgctat ttatgcatag   1620

atcatcacgc tgcagaaatt acaaaaaaac gatttaatgc caaaaccagg gtgataggct   1680

cccctcgcca taccattttc aaacataaaa                                    1710
```

```
<210> SEQ ID NO 11
<211> LENGTH: 294
<212> TYPE: PRT
<213> ORGANISM: Legionella pneumophila

<400> SEQUENCE: 11

Pro Val Leu Ile Ala Ala Gly Tyr Glu Val Arg Cys Ala Val Trp Gln
1               5                   10                  15

Lys Asn Gln Tyr Met Ser Val Glu Gln Val Glu Ile Asp Lys Leu Glu
            20                  25                  30

Gln Val Thr Asp Gly Ser Glu Ala Leu Asn Gly Ile Asp Ile Val Ile
        35                  40                  45

His Leu Ala Ala Arg Val His Val Met Arg Glu Asp Thr Ser Ser Ser
    50                  55                  60

Leu Glu Glu Tyr Cys Lys Ile Asn Ser Ile Ala Thr Lys Asn Phe Ala
65                  70                  75                  80

Gln Gln Ala Ala Lys His Lys Val Lys Arg Phe Val Phe Leu Ser Thr
                85                  90                  95
```

-continued

```
Ile Lys Val Asn Gly Glu Val Ser Leu Pro Gln Ser Pro Phe Ser Glu
            100                 105                 110

Lys Asn Ser Ala Gln Pro Lys Asp Ser Tyr Ala Gln Ser Lys Leu Glu
        115                 120                 125

Ala Glu Leu Tyr Leu Arg Glu Ile Ser Glu Asn Ser Asp Met Glu Val
    130                 135                 140

Val Ile Leu Arg Pro Pro Leu Val Tyr Gly Pro Gly Val Lys Ala Asn
145                 150                 155                 160

Phe Leu Lys Leu Leu Gly Met Val Gln Lys Gly Trp Pro Leu Pro Phe
                165                 170                 175

Ala Ser Ile Lys Asn Lys Arg Ser Phe Ile Phe Ile Asp Asn Leu Val
            180                 185                 190

Ser Ala Ile Leu Met Val Met Thr His Pro Lys Ala Ala Asn Gln Leu
        195                 200                 205

Tyr Leu Val Ala Asp Asn Glu Ser Trp Ser Leu Ala Asp Leu Leu Ser
    210                 215                 220

Leu Leu Ala Gln Asn Met Lys Ile Asn Leu Arg Leu Tyr His Phe Pro
225                 230                 235                 240

Thr Thr Phe Leu Ala Gly Leu Phe Lys Ile Thr Gly Met Gly Ser Leu
                245                 250                 255

Asn Thr Arg Leu Leu Ser Ser Leu Glu Ile Asp Ser Ser Lys Ile Ile
            260                 265                 270

Ser Asp Leu Gly Trp Thr Pro Pro Val Asp Ser Cys Glu Gly Leu Lys
        275                 280                 285

Lys Thr Ala Asp Trp Phe
    290


<210> SEQ ID NO 12
<211> LENGTH: 294
<212> TYPE: PRT
<213> ORGANISM: Legionella pneumophila

<400> SEQUENCE: 12

Pro Ala Leu Leu Ser Glu Gly His Asp Val Arg Cys Ala Val Leu Gln
1               5                   10                  15

Leu Asp Ser Thr Leu Gln Ala Glu Gln Ile Val Ile Asn Asn Leu Glu
            20                  25                  30

Val His Thr Asp Trp Thr Asp Ala Leu Arg Asn Val Glu Ile Val Ile
        35                  40                  45

His Leu Ala Ala Arg Val His Ile Met Lys Glu Tyr Val Thr Ser Cys
    50                  55                  60

Leu Asp Glu Tyr Cys Lys Ile Asn Ser Ile Ala Thr Lys Asn Phe Ala
65                  70                  75                  80

Glu Gln Ala Ala Gln Asn Asn Val Lys Arg Phe Ile Phe Leu Ser Thr
                85                  90                  95

Ile Lys Val His Gly Glu Phe Ser Gln Asn Ser Leu Pro Phe Ser Glu
            100                 105                 110

Asp Cys Arg Thr Gln Pro Glu Asp Pro Tyr Ala Lys Ser Lys Leu Phe
        115                 120                 125

Ala Glu Gln Tyr Ile Gln Glu Ile Cys Gln Asn Thr Arg Met Asp Phe
    130                 135                 140

Val Ile Leu Arg Pro Pro Leu Val Tyr Gly Pro Tyr Val Lys Ala Asn
145                 150                 155                 160

Phe Leu Lys Met Leu Gln Leu Val Asp Lys Lys Trp Pro Leu Pro Phe
                165                 170                 175
```

-continued

```
Gly Ser Ile Tyr Asn Lys Arg Thr Phe Ile Tyr Ile Asp Asn Leu Val
            180                 185                 190

Ser Ala Ile Ser Ala Val Val Arg Glu Pro Asn Ala Ala Asn Gln Ile
        195                 200                 205

Tyr Leu Val Ala Asp Asp Val Ser Trp Ser Leu Thr Gln Leu Met Gln
    210                 215                 220

Thr Leu Ser Arg Arg Met Asn Val Lys Leu Phe Leu Ile Pro Ile Pro
225                 230                 235                 240

Val Gln Ile Leu Ile Phe Leu Phe Lys Leu Cys Gly Leu Lys Asn Ile
                245                 250                 255

Asn Thr Arg Leu Phe Ser Ser Leu Glu Val Ser Asn Lys Lys Ile Lys
            260                 265                 270

Ser Gln Leu Gly Trp Thr Pro Pro Val Ser Ser Val Glu Gly Leu Glu
        275                 280                 285

Lys Thr Val Lys Trp Tyr
    290
```

MARKERS FOR DETECTION OF *LEGIONELLA PNEUMOPHILA* STRAINS

This application is the national phase of PCT application PCT/NL2009/050391 having an international filing date of 5 Jul. 2009, which claims benefit of European application No. 08159457.4 filed 1 Jul. 2008.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 313632011400Seqlist.txt | Feb. 7, 2011 | 23,502 bytes |

FIELD OF THE INVENTION

The invention relates to a method of identifying *Legionella pneumophila* strains, and in particular to a method of identifying a *Legionella pneumophila* strain as belonging to serogroup 1 or another serogroup. The invention further relates to markers for such an assay and a kit of parts comprising an array with said markers and reference materials for performing a method of the invention.

BACKGROUND OF THE INVENTION

Legionnaires' disease is an acute pneumonic illness caused by Gram-negative bacilli of the genus *Legionella*, the most common of which is *Legionella pneumophila.*

Legionnaires' disease is initiated by inhalation, and probably microaspiration, of *Legionella* bacteria into the lungs. Although *Legionella* bacteria are ubiquitous in our environment, they rarely cause disease. A number of factors must occur simultaneously before legionnaires' disease is possible. These factors include the presence of virulent strains in an environmental site; a means for dissemination of the bacteria, such as by aerosolization; and proper environmental conditions allowing the survival and inhalation of an infectious dose of the bacteria by a susceptible host.

Water contaminated with a sufficient concentration of virulent *Legionella* bacteria can be aerosolized by water-cooled heat rejection devices such as air conditioning cooling towers, whirlpool spas, shower heads, water misters, and the like. Once the bacteria enter the lung, they are phagocytosed by alveolar macrophages and then grow intracellularly. The *Legionella* bacteria produce virulence factors that enhance phagocytosis. After sufficient intracellular growth, the bacteria kill the macrophage, escape into the extracellular environment and are then rephagocytosed by other macrophages. Within a few days after initial infection, the bacterial concentration in the lung increases considerably. The resulting infiltration of the alveoli by neutrophils, additional macrophages and erythrocytes results in capillary leakage and edema and the chemokines and cytokines released by the macrophages help trigger a severe inflammatory response, which may be fatal.

More than 49 different *Legionella* species, encompassing 70 serogroups, have been described since its first discovery in 1977, 20 of which have been reported to infect humans. *L. pneumophila* contains at least 16 different serogroups. *L. pneumophila* serogroup 1 caused the 1976 Philadelphia outbreak and is the cause of 70% to 90% of all cases of legionnaires' disease. In the major outbreaks such as those originating in Bovenkarspel, The Netherlands in 1999, in Barrow-in-Furness in Cumbria, England in 2002 and near Harnes in Pas-de-Calais, France in 2003/2004, serogroup 1 strains could be detected in the majority of the patients.

*L. pneumophila* serogroup 1 can be further divided into multiple subtypes using a variety of serologic, other phenotypic and genetic methods. One particular subtype of *L. pneumophila* serogroup 1 causes the majority of cases of legionnaires' disease due to *L. pneumophila*, and 85% of the cases due to *L. pneumophila* serogroup 1; this subtype is distinguished by its reactivity with a particular monoclonal antibody, and it is variously termed Pontiac, the Joly monoclonal type 2 (MAb2), or the Dresden monoclonal type 3/1 (MAb 3/1) monoclonal subtype.

Most clinical microbiology laboratories are capable of identifying *Legionella* bacteria to the genus level by detection of their typical colony morphology, Gram stain appearance, and various other standard microbiology identification techniques. Identification of *L. pneumophila* serogroup 1, the most common clinical isolate can be accomplished by sophisticated clinical microbiology laboratories using relative simple serologic testing. However, it should be stressed that serogroup 1 strains are not the only virulent serotypes Identification of other *L. pneumophila* serogroups, and other *Legionella* species, is often much more difficult. This is because these bacteria are relatively inert in the use of commonly tested biochemical substrates, and they require sophisticated phenotypic, serologic and molecular testing. Reference laboratory-based phenotypic testing of bacteria, including determination of fatty-acids and ubiquinones and protein electrophoresis, can often be used to identify the bacteria. Definitive identification is based on both immunologic detection of surface antigens and bacterial DNA sequencing. Also, DNA typing by pulsed field electrophoresis of DNA restriction fragments is useful for identification purposes.

Diagnosis of the infecting agent from sample material (such as water that is suspected of contamination, or of clinical samples) on selective media is currently the most reliable means of diagnosis. However, cultivation is slow. Direct fluorescent antibody (DFA) stains for the visualization of *Legionella* species in clinical specimens are commercially available for a limited number of species. Assays for the detection of *L. pneumophila* serogroup 1 antigen in urine have a sensitivity of 70% and a specificity of nearly 100%. Also, an immunochromatographic assay for the rapid qualitative detection of *L. pneumophila* serogroup 1 antigen (*Legionella* NOW; Binax, Portland, Me.) in urine specimens has become available that uses rabbit anti-*L. pneumophila* serogroup 1 antibody as the capture component and rabbit anti-*L. pneumophila* serogroup 1 antibody conjugated to colloidal gold as the detection component. The assay provides a test result in 15 min and is intended to aid in the presumptive diagnosis of Legionnaires' disease caused by *L. pneumophila* serogroup 1 in conjunction with culture and other methods. Preliminary performance data for the immunochromatographic assay report a sensitivity of 95% and a specificity of 95%. Thus, so far, commercially available tests for *Legionella* urinary antigen detect only *L. pneumophila* serogroup 1, while the specificity of the assays cannot prevent the occurrence of false positive and false negative reactions.

DNA probe techniques, which produce fewer false positive reactions then immunological detection methods, may be used to detect the presence of one or more multiple *Legionella* species. However, a drawback of such DNA methods is that they cannot differentiate between virulent and non-virulent strains, presumably because the virulence trait is multi-genic. Further, they are not able to adequately identify *Legionella* strains if more than one strain is present in the sample.

Following severe outbreaks, many national authorities have implemented legislation and water quality standards for water supplies and/or codes of practice for management and operation of cooling towers and warm water storage facilities. Such standards and codes require frequent monitoring of drinking water distribution systems and swimming-pool water facilities, and upon exceeding a certain number of *Legionella* bacteria per liter, rigorous measures are taken, such as closure and evacuation of hotels, sports facilities or nursing homes. Most experts however, consider that a large number of *Legionella* bacteria detected are harmless and non-virulent. However, there is at present no assay system available, except for the tedious assay involving culturing of individual bacteria, which takes about 7 days, to correctly identify possible harmful strains if more than one bacterial strain is present in the sample. The availability of a test that is capable of reliably detecting DNA markers from a specific single *Legionella* strain would be highly favorable.

It is an object of the present invention to provide for a method capable of identifying multiple strains of *L. pneumophila*, and especially to discriminate between serogroup 1 strains, strains within this serogroup 1 and strains from other serogroups.

SUMMARY OF THE INVENTION

The present inventors have now found a method for identifying serogroup 1 *Legionella* strains from non-serogroup 1 strains. The method involves a hybridization assay with specific genetic markers. The inventors further have been able to discriminate between subgroups in the serogroup 1 strains.

In one embodiment of the present invention, the group of molecular markers comprises the marker 11B3, indicated in SEQ ID NO:1 or sequences which are highly homologous therewith.

In a further embodiment of the method of the present invention, the group of molecular markers comprises the 8 markers (5G5, 9G2, 8E11, 30A9, 9F12, 35C6, 7C10 and 12A12) indicated in SEQ ID NO:N2 to SEQ ID NO: 10, or homologues thereof.

In a further embodiment of the method of the present invention, the sample nucleic acid is derived from a mixed culture of *Legionella pneumophila*. Alternatively, the sample can be derived from any medium which is suspected of *Legionella* infestation, such as aqueous samples from water pipes, surface water, drink water, showers, baths, fountains, etc.

In a specific embodiment, a method of the invention is used for determining the presence of a plurality of *Legionella* strains, the method involving a hybridization assay with at least two specific genetic markers selected from the group of markers as depicted in SEQ ID NO:1-SEQ ID NO:10 or homologues thereof, wherein said markers are specific for a different strain.

A kit of parts, said kit comprising an array as defined herein together with reference nucleic acids as defined herein. Preferably, said kit also comprises software to calculate the result of the test.

Further part of the invention is the protein sequence of marker 11B3 and an antibody based diagnostic system for the detection thereof.

DETAILED DESCRIPTION OF THE INVENTION

The term "*Legionella pneumophila* strain" as used herein refers to the descendants of a single isolate of *Legionella pneumophila* cells in pure culture and to a taxonomic level of said pure culture below the level of the species *Legionella pneumophila.*

The term "pathogenic" in relation to a *Legionella* strain refers to a microorganism capable of causing disease (including infection) or morbid symptoms in humans or other animal hosts.

The term "array" refers to an array of individual fragments of DNA or oligonucleotides that are bound to a substrate such as a microscope slide. The purpose of an array experiment is to determine the amount of matching nucleic acid fragments in a particular sample. The target nucleic acid fragments are extracted from the cells or tissues of interest, optionally converted to DNA, and labeled. They are then hybridized to all the DNA or oligonucleotide spots on the array. Matches (i.e. the spots where hybridization has taken place) are identified using antibody detection, optionally combined with precipitation, chromatography, colorimetry, and/or phosphorescent or fluorescent imaging. The data resulting from an array experiment are a list of measurements of spot intensities. A preferred array of the invention is an array which has less than 1000, preferably less than 100, more preferably less than 10 spots, and which contains at least the DNA sequences of SEQ ID NO:1 and SEQ ID NO:2 Another preferred array of the invention is an array which has less than 1000, preferably less than 100, more preferably less than 10 spots, and which contains at least five sequences selected from the sequences as presented in SEQ ID NO:1 through SEQ ID NO:10, with the proviso that the number of spots is at least equal to the number of sequences that the array comprises.

The term "nucleic acid" as used herein, is interchangeable with the term "polynucleotide", and refers to a nucleotide multimer or polymeric form of nucleotides having any number of nucleotides, e.g., deoxyribonucleotides or ribonucleotides, or compounds produced synthetically (e.g. PNA as described in U.S. Pat. No. 5,948,902 and the references cited therein) and can be either double- or single-stranded. A polynucleotide can hybridize with other polynucleotides in a sequence specific manner, e.g. can participate in Watson-Crick base pairing interactions. The term also includes modified, for example by methylation and/or by capping, and unmodified forms of the polynucleotide The terms "deoxyribonucleic acid" and "DNA" as used herein mean a polymer composed of deoxyribonucleotides.

The term "oligonucleotide" refers to a short sequence of nucleotide monomers (usually 6 to 100 nucleotides) joined by phosphorous linkages (e.g., phosphodiester, alkyl and aryl-phosphate, phosphorothioate), or non-phosphorous linkages (e.g., peptide, sulfamate and others). An oligonucleotide may contain modified nucleotides having modified bases (e.g., 5-methyl cytosine) and modified sugar groups (e.g., 2'-O-methyl ribosyl, 2'-O-methoxyethyl ribosyl, 2'-fluoro ribosyl, 2'-amino ribosyl, and the like). Oligonucleotides may be naturally-occurring or synthetic molecules of double- and single-stranded DNA and double- and single-stranded RNA with circular, branched or linear shapes and optionally including domains capable of forming secondary structures (e.g., stem-loop, pseudo knots and kissing loop structures).

The term "nucleotide sequence homology" as used herein denotes the presence of homology between two polynucleotides. Polynucleotides have "homologous" sequences if the sequence of nucleotides in the two sequences is the same when aligned for maximum correspondence. Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence homology" for polynucleotides, such as 50, 60, 70, 80, 90, 95, 98, 99 or 100 percent sequence homology may be determined by comparing two optimally aligned sequences over a comparison window, wherein the portion of the polynucleotide sequence in the comparison window may include additions or deletions (i.e. gaps) as compared to the reference sequence (which does not comprise additions or deletions) for optimal alignment of the two sequences. The percentage is calculated by: (a) determining the number of positions at which the identical nucleic acid base occurs in both sequences to yield the number of matched positions; (b) dividing the number of matched positions by the total number of positions in the window of comparison; and (c) multiplying the result by 100 to yield the percentage of sequence homology. Optimal alignment of sequences for comparison may be conducted by computerized implementations of known algorithms, or by visual inspection. Readily available sequence comparison and multiple sequence alignment algorithms are, respectively, the Basic Local Alignment Search Tool (BLAST) (Altschul et al., 1990; Altschul et al., 1997) and ClustalW programs, both available on the internet. Other suitable programs include, but are not limited to, GAP, BestFit, PlotSimilarity, and FASTA in the Wisconsin Genetics Software Package (Genetics Computer Group (GCG), Madison, Wis., USA) (Devereux et al., 1984).

As used herein, "substantially complementary" means that two nucleic acid sequences have at least about 70%, preferably about 80%, more preferably about 90%, even more preferably 95%, and most preferably about 98%, sequence complementarity to each other. This means that primers and probes must exhibit sufficient complementarity to their template and target nucleic acid, respectively, to hybridise under stringent conditions. Therefore, the primer and probe sequences need not reflect the exact complementary sequence of the binding region on the template and degenerate primers can be used. For example, a non-complementary nucleotide fragment may be attached to the 5'-end of the primer, with the remainder of the primer sequence being complementary to the strand. Alternatively, non-complementary bases or longer sequences can be interspersed into the primer, provided that the primer has sufficient complementarity with the sequence of one of the strands to be amplified to hybridize therewith, and to thereby form a duplex structure which can be extended by the polymerising means. The non-complementary nucleotide sequences of the primers may include restriction enzyme sites. Appending a restriction enzyme site to the end(s) of the target sequence would be particularly helpful for cloning of the target sequence. A substantially complementary primer sequence is one that has sufficient sequence complementarity to the amplification template to result in primer binding and second-strand synthesis. The skilled person is familiar with the requirements of primers to have sufficient sequence complementarity to the amplification template.

The term "hybrid" in the context of nucleic acids refers to a double-stranded nucleic acid molecule, or duplex, formed by hydrogen bonding between complementary nucleotide bases. The terms "hybridise" or "anneal" refer to the process by which single strands of nucleic acid sequences form double-helical segments through hydrogen bonding between complementary bases.

The term "probe" refers to a single-stranded oligonucleotide sequence that will recognize and form a hydrogen-bonded duplex with a complementary sequence in a target nucleic acid sequence analyte or its cDNA derivative.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerisation such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerisation. The exact lengths of the primers will depend on many factors, including temperature and composition (A/T en G/C content) of primer. A pair of bi-directional primers consists of one forward and one reverse primer as commonly used in the art of DNA amplification such as in PCR amplification.

It will be understood that "primer", as used herein, may refer to more than one primer, particularly in the case where there is some ambiguity in the information regarding the terminal sequence(s) of the target region to be amplified. Hence, a "primer" includes a collection of primer oligonucleotides containing sequences representing the possible variations in the sequence or includes nucleotides which allow a typical base pairing.

The oligonucleotide primers may be prepared by any suitable method. Methods for preparing oligonucleotides of specific sequence are known in the art, and include, for example, cloning and restriction of appropriate sequences, and direct chemical synthesis. Chemical synthesis methods may include, for example, the phospho di- or tri-ester method, the diethylphosphoramidate method and the solid support method disclosed in e.g. U.S. Pat. No. 4,458,066. The primers may be labelled, if desired, by incorporating means detectable by for instance spectroscopic, fluorescence, photochemical, biochemical, immunochemical, or chemical means.

Template-dependent extension of the oligonucleotide primer(s) is catalysed by a polymerising agent in the presence of adequate amounts of the four deoxyribonucleotide triphosphates (dATP, dGTP, dCTP and dTTP, i.e. dNTPs) or analogues, in a reaction medium which is comprised of the appropriate salts, metal cations, and pH buffering system. Suitable polymerizing agents are enzymes known to catalyse primer- and template-dependent DNA synthesis. Known DNA polymerases include, for example, *E. coli* DNA polymerase I or its Klenow fragment, T4 DNA polymerase, and Taq DNA polymerase. The reaction conditions for catalysing DNA synthesis with these DNA polymerases are known in the art.

The products of the synthesis are duplex molecules consisting of the template strands and the primer extension strands, which include the target sequence. These products, in turn, serve as template for another round of replication. In the second round of replication, the primer extension strand of the first cycle is annealed with its complementary primer; synthesis yields a "short" product which is bound on both the 5'- and the 3'-ends by primer sequences or their complements. Repeated cycles of denaturation, primer annealing and extension result in the exponential accumulation of the target region defined by the primers. Sufficient cycles are run to achieve the desired amount of polynucleotide containing the target region of nucleic acid. The desired amount may vary, and is determined by the function which the product polynucleotide is to serve.

The PCR method is well described in handbooks and known to the skilled person.

After amplification by PCR, the target polynucleotides may be detected by hybridisation with a probe polynucleotide which forms a stable hybrid with that of the target sequence under stringent to moderately stringent hybridisation and wash conditions. If it is expected that the probes will be essentially completely complementary (i.e., about 99% or greater) to the target sequence, stringent conditions will be used. If some mismatching is expected, for example if variant strains are expected with the result that the probe will not be completely complementary, the stringency of hybridisation may be lessened. However, conditions are chosen which rule out non-specific/adventitious binding. Conditions which affect hybridisation, and which select against non-specific binding are known in the art, and are described in, for example, Sambrook et al., (2001). Generally, lower salt concentration and higher temperature increase the stringency of binding. For example, it is usually considered that stringent conditions are incubations in solutions which contain approximately 0.1×SSC, 0.1% SDS, at about 65° C. incubation/wash temperature, and moderately stringent conditions are incubations in solutions which contain approximately 1-2×SSC, 0.1% SDS and about 50°-65° C. incubation/wash temperature. Low stringency conditions are 2×SSC and about 30°-50° C.

The terms "stringency" or "stringent hybridisation conditions" refer to hybridisation conditions that affect the stability of hybrids, e.g., temperature, salt concentration, pH, formamide concentration and the like. These conditions are empirically optimised to maximize specific binding and minimize non-specific binding of primer or probe to its target nucleic acid sequence. The terms as used include reference to conditions under which a probe or primer will hybridise to its target sequence, to a detectably greater degree than other sequences (e.g. at least 2-fold over background). Stringent conditions are sequence dependent and will be different in different circumstances. Longer sequences hybridise specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridises to a perfectly matched probe or primer. Typically, stringent conditions will be those in which the salt concentration is less than about 1.0 M Na+ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridisation with a buffer solution of 30% formamide, 1 M NaCl, 1% SDS at 37° C. and a wash in 2×SSC at 40° C. Exemplary high stringency conditions include hybridisation in 50% formamide, 1 M NaCl, 1% SDS at 37° C., and a wash in 0.1×SSC at 60° C. Hybridisation procedures are well known in the art and are described by e.g. Ausubel et al., 1998 and Sambrook et al., 2001.

The term "fragmented genomic DNA" refers to pieces of DNA of the genome of a cell that are the result of the partial physical, chemical or biological break-up of the lengthy DNA into discrete fragments of shorter length.

The term "hybridization pattern" refers to the list of measurements of spot intensities obtained after hybridizing the array with a target nucleic acid.

The term "nucleotide" is used to denote a deoxyribonucleoside, a ribonucleoside, or a 2'-O-substituted ribonucleoside residue The term "molecular marker" generally refers to markers identifying variation at the level of DNA and is herein used to refer to a mutation (of any type) or nucleotide sequence which has a scorable or selectable relation with the phenotype of serogroup 1 or any other serogroups, or with any special subgroup within a serogroup. (and hence can "mark" a region of the chromosome). The term "protein marker" refers to proteins that can be used for the identification of an organism or for detection of a the state of an organism.

An 'incompatible marker pair' is a pair of markers that together enables separation in two groups. This means that marker 1 is present in all individuals of group 1 and is absent from all individuals in group 2 whereas marker 2 is absent from all individuals from group 1 but present in all individuals from group 2. In this way the combined analysis of markers 1 and 2 will always lead to an assignment to group 1 or group 2. A sample which is positive for both markers 1 and 2 therefore indicates a mixture of two individuals of the two groups. In the present invention an incompatible marker pair is a pair of markers of which one member is specific for one serogroup or subgroup within a serogroup of *Legionella*, while the other member of the pair of markers is specific for the rest of the serogroup(s) or subserogroup(s Now, a marker, designated 11B3 (SEQ ID NO: 1) has been found, that is specific for *Legionella* subgroups 2-14 and which does not occur in subgroup 1. In this way, it can be used as a marker discriminating bacteria from subgroup 1 from bacteria from the other subgroups. Conversely, a marker designated 19H4 (SEQ ID NO: 10) has been found which is specific for serogroup 1. Thus, if a mixture of *Legionella* strains is present in a sample, it can easily be detected whether such a sample harbours members of the serogroup 1 phenotype and/or of other serogroup phenotypes.

Next, it has also been shown to be possible to find incompatible marker pairs within serogroup 1. A first example is the pair of markers formed by marker 5G5 (SEQ ID NO: 2), which is unique for a sub-serogroup in serogroup 1, designated 1A and any of the markers 9G2 (SEQ ID NO: 3), 8E11 (SEQ ID NO: 4) and 30A9 (SEQ ID NO: 5) that are unique for a second subserogroup in serogroup 1, designated 1B. Of the three markers for serogroup 1B, the marker 9G2 is preferred. Thus, even if a sample only harbours bacteria of serogroup I, it is still possible to discriminate whether there is more than one strain of this serogroup 1 in the sample if these more than one strains belong to different subgroups.

Further, as will be shown in the experimental section, incompatible marker pairs are the pairs 9F12-35C6, 24D9-25B6 and 7C10-12A12.

A detection whether a test sample contains multiple species of *Legionella* would be feasible with the above described markers. Such a detection would be fast and reliable, since only minor amounts of sample material are needed to perform the hybridization tests and thus no culturing of the bacterial strains has to be performed. Further, hybridization tests are reliable and, as is shown in the examples, the tests with the above described markers give robust results.

In another embodiment of the present invention, the array comprises at least three, at least five, at least seven of the nine sequences as depicted in SEQ ID NO:1 through SEQ ID NO:10 or all of these ten sequences. The sequences of markers given in the sequence listing are about 1k nucleotides long. However, this does not necessarily mean that the complete sequence as shown in any of the SEQ ID's needs to be present on the array: the assay can be been performed with sequences, which are parts thereof. It should, however, be understood, that a minimal length is necessary for obtaining a correct and distinctive hybridization with any sample nucleic acid. Thus, the length of these part(s) of the sequences should range from about 50 to about 2000 nucleotides, i.e. the sequences can be shorter or longer than those presented in the sequence listing, but for a sufficient hybridization to occur they should be at least 50 nucleotides long. Longer sequences than those depicted can be obtained by hybridizing the genome from a *Legionella* species and, if hybridization occurs with the presented sequence, excising a larger part of the sequence from the genomic DNA.

Further, hybridization allows for some mismatches between the sequence on the array and the nucleotide sequence of the sample. Therefore, any nucleotide sequence or part thereof (as defined above) which has a homology of at least 70%, preferably at least 80%, more preferably at least 90%, more preferably at least 95%, even more preferably at least 98% with the sequences of SEQ ID NO: 1 through SEQ ID NO: 9 is applicable in and intended within the scope of the present invention.

In the current invention the term "homologues" is used to indicate both (parts of) the sequences of the invention of at least 50, but preferably at least 100, more preferably at least 200, more preferably at least 500 and most preferably at least 1000 nucleotides, and sequences which have a degree of homology of at least 70%, preferably at least 80%, more preferably at least 90%, more preferably at least 95%, even more preferably at least 98% with the sequences of SEQ ID NO:1 through SEQ ID NO:10. More specifically, a homologue of SEQ ID NO:1 will have a degree of homology of at least 90%, more preferably 95% or 98% over a stretch of 200 nucleotides taken from SEQ ID NO:1, more preferably said homologue will have a degree of homology of at least 80%, more preferably 90%, 95% or 98% over a stretch of 500 nucleotides taken from SEQ ID NO:1, and most preferably said homologue will have a degree of homology of at least 70%, more preferably 80%, 90%, 95% or 98% over a stretch of 700 nucleotides. Homologues of any of the sequences SEQ ID NO:2 to SEQ ID NO:5 will preferably have a degree of homology of at least 85%, more preferably 90%, 95% or 98% over a stretch of 500 nucleotides taken from said SEQ ID NO.

The above discussed markers, or fragments thereof may be spotted on a surface to provide for a DNA micro-array. In order to facilitate coupling of the fragments, the surface of the array (e.g. the slide, the surface of which may i.a. be glass, gold, etc.) may be modified. Spotting may occur by any method available, for instance by using ElectroSpray Ionization (ESI) micro-array printing. After spotting of the markers or fragments thereof, the slide surfaces may be blocked to prevent further attachment of nucleic acids, e.g. by treatment with boro-anhydride in case of formaldehyde modified glass-slide surfaces.

To facilitate detection of successful hybridization, the gDNA is suitably labeled, preferably with a compound which is uniquely detectable by an antibody. Such a compound can for instance be biotin. Labeling of nucleotides with biotin and subsequent detection through antibodies specific for biotin, has been sufficiently described in the literature and will be routine experimentation for a person skilled in the art. Alternatively, the nucleotides are fluorescently labeled (e.g. by using Cy™ labels [Amersham Pharmacia Biotech]). Fluorescent labeling kits are commercially available from various manufacturers. In order to be able to judge the signals caused by the hybridization of the marker sequences with sample nucleic acid, preferably the array also comprises reference nucleotide sequences, which can serve as positive and negative controls. As negative controls, sequences should be used of about the same length as the average length of the markers, but which will not hybridize with any nucleotide sequence in the sample, i.e. sequences, which do not occur in *Legionella*. As positive control, a sequence should be used which will be present in (nearly) all samples to be tested. For this purpose preferably the *Legionella* 30S ribosomal protein S21 (Cazalet, C., Rusniok, C., Bruggemann, H., Zidane, N., Magnier, A., Ma, L., Tichit, M., Jarraud, S., Bouchier, C., Vandenesch, F., Kunst, F., Etienne, J., Glaser, P. and Buchrieser, C. Nat. Genet. 36 (11), 1165-1173 (2004)) or a conserved sequence of one of the housekeeping enzymes should be used.

The average size of sample nucleic acid has an effect on the signal distribution on the array. Larger sample molecules comprise more information and are thus more likely to find a suitable hybridization partner in more of the spots. Reducing the average size of the sample nucleic acid can reduce this phenomenon. On the other hand, when the sample nucleic acid is too small, the nucleic acid fragments in the sample contain too little genetic information and also find suitable hybridization partners in many spots. The average size of the fragments in the sample nucleic acid is preferably between about 30 and 3000 nucleotides. More preferably, the average size of the fragments in the sample nucleic acid comprises a size of between about 50 and 1000 nucleotides, more preferably between about 100 and 500 nucleotides.

In a method for detecting a *L. pneumophila* strain, the sample nucleic acid may represent the whole or a part of the sample genome. Preferably, at least those parts of the genome are present in which the presence of molecular markers as defined herein is to be detected. This can be achieved by randomly digestion of the genomic DNA of the sample to fragments of about 1.5 kb or by physically fragmenting the DNA (e.g. by shearing) to form fragments of about that size. In a preferred embodiment a PCR amplification step is performed on either the intact genomic DNA or on the fragmented DNA with primers that specifically cause amplification of one or more of the sequences of the invention. Alternatively, the DNA can be randomly (primer) labeled using Klenow DNA polymerase (BioPrime kit Invitrogen) according to the manufacturer's instructions.

The fragmented sample DNA is then brought into contact with the array of the invention, which contains at least the two marker sequences of SEQ ID NO:1 and SEQ ID NO:10 or fragments thereof, or homologues of said markers or fragments thereof. In addition or alternatively the array comprises at least one of the following combinations of two marker sequences: SEQ ID NO:2 and SEQ ID NO:3; SEQ ID NO:2 and SEQ ID NO:4; SEQ ID NO:2 and SEQ ID NO:5; SEQ ID NO:6 and SEQ ID NO:7; SEQ ID NO:8 and SEQ ID NO:9, or fragments thereof, or homologues of said markers or fragments thereof. Hybridization of the sample nucleotides with the marker sequences and the hybridization signals with optional positive and negative control sequences is then determined.

Since it was found that SEQ ID NO:1 (marker 11B3) is (part of) a coding sequence, it is also possible to use the protein that is encoded by this sequence as a protein marker that is specific for *L. pneumophila* subgroups 2-12. In the sequence of 11B3 given below the start and stop of the protein sequence that is also given is indicated. Please note that the nucleotide sequence is the complement of the coding sequence. As can be derived from the sequence alignment given below between the partial amino acid sequence encoded by (the complement of) SEQ ID NO:1 and the hypothetical protein 1p10798 of the serogroup I strain *L. pneumophila* str. Lens, both proteins share some parts that are conserved, but in other areas many differences can be found. It is of course necessary for an assay based on the protein that such an assay would focus on these differences to be able to discriminate between serogroups. In a preferred embodiment antibodies that are specific for those areas that differ between the proteins (such as the areas of amino acids 17-45, 56-66, 103-144, 220-246 and 266-274 of SEQ ID NO:11 and SEQ ID NO:12) are used in an immunoassay to specifically bind to and detect the protein. It is submitted that based on the sequence information provided herein, a person skilled in the art will be able to produce antibodies that are specific for the amino acid sequence of SEQ ID NO:11 and the amino acid sequence of SEQ ID NO:12 (the protein from serogroup 1). Also the use of such specific antibodies in an immunoassay to detect the presence or absence of the proteins is well known in the art.

EXAMPLES

DNA Isolation of Sample

In the present Example a total of 144 samples from different strains were selected from the collection of strains of the Streeklaboratorium Kennemerland in Haarlem, The Netherlands. Of these 144 samples, a total of 74 samples were isolated from hospital patients (pathogenic or clinical strains) and a total of 70 samples was isolated from industrial and public water supply systems, and were not detected in humans (environmental strains).

Labeling and Hybridisation of Genomic DNA

All strains were cultivated after which genomic DNA was isolated from these strains. The DNA was then randomly (primer) labeled using Klenow DNA polymerase (BioPrime kit Invitrogen) according to the manufacturer's instructions.

Cy3 labeled marker sequences were prepared. The DNA sample consisted of the DNA of the test strain and was labeled with Cy5. Both labeled samples were hybridized simultaneously to a microarray. Upon scanning and image analysis, the ratio of the Cy5/Cy3 emission values was calculated for each spot on the microarray. These ratio's served as data input for further data analysis. Table 1 shows the results obtained in this assay, where 1 indicates the presence of the marker in the sample and 0 indicates the absence of the marker in the sample. It can be observed that the markers are specific for one or more serotypes.

TABLE 1

Presence or absence of incompatible marker pairs in a set of 144 *L. pneumophila* isolates

| Strain | Serotype | 019H4 | 011B3 | 005G5 | 009G2 | 008E11 | 030A9 | 009F12 | 035C6 | 007C10 | 012A12 |
|---|---|---|---|---|---|---|---|---|---|---|---|
| TTC 04.0222 | 7–>14 | 0 | 1 | 0 | 1 | 1 | 1 | 0 | 1 | 0 | 1 |
| TTC 04.0222 | 7–>14 | 0 | 1 | 0 | 1 | 1 | 1 | 0 | 1 | 0 | 1 |
| TTC 04.0222 | 7–>14 | 0 | 1 | 0 | 1 | 1 | 1 | 0 | 1 | 0 | 1 |
| TTC 04.0224 | 6 | 0 | 1 | 1 | 0 | 0 | 0 | 0 | 1 | 0 | 1 |
| TTC 04.0223 | 7–>14 | 0 | 1 | 1 | 0 | 0 | 0 | 0 | 1 | 0 | 1 |
| TTC 04.0223 | 7–>14 | 0 | 1 | 1 | 0 | 0 | 0 | 0 | 1 | 0 | 1 |
| TTC 04.0223 | 7–>14 | 0 | 1 | 1 | 0 | 0 | 0 | 0 | 1 | 0 | 1 |
| TTC 04.0226 | 5 | 0 | 1 | 1 | 0 | 0 | 0 | 0 | 1 | 0 | 1 |
| TTC 04.0228 | 3 | 0 | 1 | 1 | 0 | 0 | 0 | 0 | 1 | 0 | 1 |
| TTC 04.0227 | 5 | 0 | 1 | 1 | 0 | 0 | 0 | 0 | 1 | 0 | 1 |
| TTC 04.0225 | 6 | 0 | 1 | 1 | 0 | 0 | 0 | 0 | 1 | 0 | 1 |
| TTC 04.0229 | 3 | 0 | 1 | 1 | 0 | 0 | 0 | 0 | 1 | 0 | 1 |
| TTC 04.0231 | 1 | 1 | 0 | 0 | 1 | 1 | 1 | 0 | 1 | 0 | 1 |
| TTC 04.0232 | 1 | 1 | 0 | 0 | 1 | 1 | 1 | 0 | 1 | 0 | 1 |
| TTC 04.0233 | 1 | 1 | 0 | 1 | 0 | 0 | 0 | 0 | 1 | 0 | 1 |
| TTC 04.0234 | 1 | 1 | 0 | 0 | 1 | 1 | 1 | 0 | 1 | 0 | 1 |
| TTC 04.0235 | 1 | 1 | 0 | 0 | 1 | 1 | 1 | 0 | 1 | 0 | 1 |
| TTC 04.0236 | 1 | 1 | 0 | 0 | 1 | 1 | 1 | 0 | 1 | 0 | 1 |
| TTC 04.0237 | 1 | 1 | 0 | 0 | 1 | 1 | 1 | 1 | 0 | 0 | 1 |
| TTC 04.0238 | 3 | 0 | 1 | 1 | 0 | 0 | 0 | 0 | 1 | 0 | 1 |
| TTC 04.0239 | 1 | 1 | 0 | 0 | 1 | 1 | 1 | 0 | 1 | 0 | 1 |
| TTC 04.0240 | 1 | 1 | 0 | 0 | 1 | 1 | 1 | 0 | 1 | 0 | 1 |
| TTC 04.0241 | 7–>14 | 0 | 1 | 1 | 0 | 0 | 0 | 0 | 1 | 0 | 1 |
| TTC 04.0242 | 7–>14 | 0 | 1 | 1 | 0 | 0 | 0 | 0 | 1 | 0 | 1 |
| TTC 05.0296 | 1 | 1 | 0 | 1 | 0 | 0 | 0 | 0 | 1 | 1 | 0 |
| TTC 05.0297 | 1 | 1 | 0 | 1 | 0 | 0 | 0 | 0 | 1 | 0 | 1 |
| TTC 05.0298 | 7–>14 | 0 | 1 | 1 | 0 | 0 | 0 | 0 | 1 | 0 | 1 |
| TTC 05.0299 | 1 | 1 | 0 | 0 | 1 | 1 | 1 | 1 | 0 | 1 | 0 |
| TTC 05.0300 | 1 | 1 | 0 | 0 | 1 | 1 | 1 | 0 | 1 | 0 | 1 |
| TTC 05.0301 | 1 | 1 | 0 | 0 | 1 | 1 | 1 | 0 | 1 | 0 | 1 |
| TTC 05.0302 | 1 | 1 | 0 | 0 | 1 | 1 | 1 | 0 | 1 | 0 | 1 |
| TTC 05.0303 | 1 | 1 | 0 | 0 | 1 | 1 | 1 | 0 | 1 | 0 | 1 |
| TTC 05.0304 | 6 | 0 | 1 | 1 | 0 | 0 | 0 | 0 | 1 | 1 | 0 |
| TTC 05.0305 | 1 | 1 | 0 | 1 | 0 | 0 | 0 | 0 | 1 | 1 | 0 |
| TTC 05.0306 | 1 | 1 | 0 | 1 | 0 | 0 | 0 | 0 | 1 | 1 | 0 |
| TTC 05.0307 | 1 | 1 | 0 | 0 | 1 | 1 | 1 | 0 | 1 | 0 | 1 |
| TTC 05.0308 | 1 | 1 | 0 | 1 | 0 | 0 | 0 | 0 | 1 | 0 | 1 |
| TTC 05.0309 | 1 | 1 | 0 | 0 | 1 | 1 | 1 | 0 | 1 | 0 | 1 |
| TTC 05.0312 | 1 | 0 | 1 | 1 | 0 | 0 | 0 | 0 | 1 | 0 | 1 |
| TTC 05.0313 | 7–>14 | 0 | 1 | 1 | 0 | 0 | 0 | 0 | 1 | 0 | 1 |
| TTC 05.0314 | 5 | 0 | 1 | 1 | 0 | 0 | 0 | 0 | 1 | 1 | 0 |
| TTC 05.0315 | 1 | 1 | 0 | 0 | 1 | 1 | 1 | 0 | 1 | 0 | 1 |
| TTC 05.0319 | 1 | 1 | 0 | 1 | 0 | 0 | 0 | 0 | 1 | 1 | 0 |
| TTC 05.0342 | 1 | 1 | 0 | 1 | 0 | 0 | 0 | 0 | 1 | 1 | 0 |
| TTC 05.0343 | 1 | 1 | 0 | 1 | 0 | 0 | 0 | 0 | 1 | 0 | 1 |
| TTC 05.0344 | 1 | 1 | 0 | 0 | 1 | 1 | 1 | 0 | 1 | 0 | 1 |
| TTC 05.0345 | 1 | 1 | 0 | 1 | 0 | 0 | 0 | 0 | 1 | 1 | 0 |

TABLE 1-continued

Presence or absence of incompatible marker pairs in a set of 144 *L. pneumophila* isolates

| Strain | Serotype | 019H4 | 011B3 | 005G5 | 009G2 | 008E11 | 030A9 | 009F12 | 035C6 | 007C10 | 012A12 |
|---|---|---|---|---|---|---|---|---|---|---|---|
| TTC 05.0346 | 1 | 1 | 0 | 0 | 1 | 1 | 1 | 1 | 0 | 0 | 1 |
| TTC 05.0347 | 1 | 1 | 0 | 1 | 0 | 0 | 0 | 0 | 1 | 1 | 0 |
| TTC 05.0348 | 7->14 | 0 | 1 | 0 | 1 | 1 | 1 | 0 | 1 | 0 | 1 |
| TTC 05.0349 | 7->14 | 0 | 1 | 1 | 0 | 0 | 0 | 0 | 1 | 1 | 0 |
| TTC 05.0350 | 1 | 1 | 0 | 1 | 0 | 0 | 0 | 0 | 1 | 1 | 0 |
| TTC 05.0351 | 1 | 1 | 0 | 0 | 1 | 1 | 1 | 0 | 1 | 0 | 1 |
| TTC 05.0372 | 1 | 1 | 0 | 1 | 0 | 0 | 0 | 0 | 1 | 0 | 1 |
| TTC 05.0316 | 1 | 1 | 0 | 1 | 0 | 0 | 0 | 0 | 1 | 1 | 0 |
| TTC 05.0376 | 5 | 0 | 1 | 1 | 0 | 0 | 0 | 0 | 1 | 1 | 0 |
| TTC 05.0377 | 3 | 0 | 1 | 1 | 0 | 0 | 0 | 0 | 1 | 0 | 1 |
| TTC 05.0378 | 2 | 0 | 1 | 1 | 0 | 0 | 0 | 1 | 0 | 1 | 0 |
| TTC 05.0379 | 5 | 0 | 1 | 0 | 1 | 1 | 1 | 0 | 1 | 0 | 1 |
| TTC 05.0380 | 1 | 1 | 0 | 0 | 1 | 1 | 1 | 1 | 0 | 1 | 0 |
| TTC 05.0381 | 7->14 | 0 | 1 | 0 | 1 | 1 | 1 | 0 | 1 | 0 | 1 |
| TTC 05.0382 | 1 | 1 | 0 | 1 | 0 | 0 | 0 | 0 | 1 | 0 | 1 |
| TTC 05.0383 | 1 | 1 | 0 | 0 | 1 | 1 | 1 | 0 | 1 | 0 | 1 |
| TTC 05.0384 | 3 | 0 | 1 | 1 | 0 | 0 | 0 | 0 | 1 | 1 | 0 |
| TTC 05.0385 | 1 | 1 | 0 | 0 | 1 | 1 | 1 | 0 | 1 | 0 | 1 |
| TTC 05.0386 | 8 | 0 | 1 | 0 | 1 | 1 | 1 | 1 | 0 | 1 | 0 |
| TTC 05.0387 | 1 | 1 | 0 | 0 | 1 | 1 | 1 | 1 | 0 | 0 | 1 |
| TTC 05.0388 | 6 | 0 | 1 | 1 | 0 | 0 | 0 | 0 | 1 | 1 | 0 |
| TTC 05.0389 | 1 | 1 | 0 | 0 | 1 | 1 | 1 | 0 | 1 | 0 | 1 |
| TTC 05.0390 | 1 | 1 | 0 | 1 | 0 | 0 | 0 | 0 | 1 | 1 | 0 |
| TTC 05.0391 | 1 | 1 | 0 | 1 | 0 | 0 | 0 | 0 | 1 | 1 | 0 |
| TTC 04.0243 | 1 | 1 | 0 | 1 | 0 | 0 | 0 | 0 | 1 | 0 | 1 |
| TTC 04.0243 | 1 | 1 | 0 | 1 | 0 | 0 | 0 | 0 | 1 | 0 | 1 |
| TTC 04.0243 | 1 | 1 | 0 | 1 | 0 | 0 | 0 | 0 | 1 | 0 | 1 |
| TTC 04.0244 | 1 | 1 | 0 | 0 | 1 | 1 | 1 | 1 | 1 | 0 | 1 |
| TTC 04.0244 | 1 | 1 | 0 | 0 | 1 | 1 | 1 | 1 | 0 | 0 | 1 |
| TTC 04.0244 | 1 | 1 | 0 | 0 | 1 | 1 | 1 | 1 | 0 | 0 | 1 |
| TTC 04.0245 | 1 | 1 | 0 | 0 | 1 | 1 | 1 | 1 | 0 | 0 | 1 |
| TTC 04.0245 | 1 | 1 | 0 | 0 | 1 | 1 | 1 | 1 | 0 | 0 | 1 |
| TTC 04.0245 | 1 | 1 | 0 | 0 | 1 | 1 | 1 | 1 | 0 | 0 | 1 |
| TTC 04.0250 | 1 | 1 | 0 | 1 | 0 | 0 | 0 | 1 | 0 | 1 | 0 |
| TTC 04.0247 | 1 | 1 | 0 | 0 | 1 | 1 | 1 | 1 | 0 | 1 | 0 |
| TTC 04.0251 | 6 | 0 | 1 | 1 | 0 | 0 | 0 | 0 | 1 | 0 | 1 |
| TTC 04.0246 | 1 | 1 | 0 | 1 | 0 | 0 | 0 | 1 | 0 | 1 | 0 |
| TTC 04.0249 | 3 | 0 | 1 | 1 | 0 | 0 | 0 | 0 | 1 | 0 | 1 |
| TTC 04.0248 | 1 | 1 | 0 | 1 | 0 | 0 | 0 | 1 | 0 | 1 | 0 |
| TTC 04.0252 | 1 | 1 | 0 | 0 | 1 | 1 | 1 | 1 | 0 | 1 | 0 |
| TTC 04.0253 | 1 | 1 | 0 | 1 | 0 | 0 | 0 | 0 | 1 | 1 | 0 |
| TTC 04.0254 | 1 | 1 | 0 | 1 | 0 | 0 | 0 | 0 | 1 | 1 | 0 |
| TTC 04.0255 | 1 | 1 | 0 | 1 | 0 | 0 | 0 | 0 | 1 | 1 | 0 |
| TTC 04.0256 | 1 | 1 | 0 | 0 | 1 | 1 | 1 | 1 | 0 | 1 | 0 |
| TTC 04.0257 | 1 | 1 | 0 | 1 | 0 | 0 | 0 | 0 | 1 | 0 | 1 |
| TTC 04.0258 | 7->14 | 0 | 1 | 0 | 1 | 1 | 1 | 0 | 1 | 0 | 1 |
| TTC 04.0259 | 1 | 1 | 0 | 1 | 0 | 0 | 0 | 0 | 1 | 0 | 1 |
| TTC 04.0260 | 1 | 1 | 0 | 0 | 1 | 1 | 1 | 1 | 0 | 0 | 1 |
| TTC 05.0266 | 1 | 1 | 0 | 0 | 1 | 1 | 1 | 0 | 1 | 0 | 1 |
| TTC 05.0267 | 1 | 1 | 0 | 1 | 0 | 0 | 0 | 0 | 1 | 0 | 1 |
| TTC 05.0268 | 1 | 1 | 0 | 0 | 1 | 1 | 1 | 1 | 0 | 0 | 1 |
| TTC 05.0269 | 1 | 1 | 0 | 1 | 0 | 0 | 0 | 0 | 1 | 1 | 0 |
| TTC 05.0270 | 1 | 1 | 0 | 1 | 0 | 0 | 0 | 0 | 1 | 1 | 0 |
| TTC 05.0271 | 3 | 0 | 1 | 1 | 0 | 0 | 0 | 0 | 1 | 0 | 1 |
| TTC 05.0272 | 1 | 1 | 0 | 0 | 1 | 1 | 1 | 1 | 0 | 0 | 1 |
| TTC 05.0273 | 1 | 1 | 0 | 1 | 0 | 0 | 0 | 0 | 1 | 1 | 0 |
| TTC 05.0274 | 1 | 1 | 0 | 0 | 1 | 1 | 1 | 1 | 0 | 1 | 0 |
| TTC 05.0275 | 1 | 1 | 0 | 1 | 0 | 0 | 0 | 0 | 1 | 0 | 1 |
| TTC 05.0276 | 1 | 1 | 0 | 0 | 1 | 1 | 1 | 1 | 0 | 1 | 0 |
| TTC 05.0277 | 1 | 1 | 0 | 1 | 0 | 0 | 0 | 1 | 0 | 1 | 0 |
| TTC 05.0278 | 1 | 1 | 0 | 1 | 0 | 0 | 0 | 1 | 0 | 1 | 0 |
| TTC 05.0279 | 1 | 1 | 0 | 0 | 1 | 1 | 1 | 1 | 0 | 0 | 1 |
| TTC 05.0280 | 1 | 1 | 0 | 0 | 1 | 1 | 1 | 1 | 0 | 1 | 0 |
| TTC 05.0281 | 6 | 0 | 1 | 1 | 0 | 0 | 0 | 0 | 1 | 0 | 1 |
| TTC 05.0282 | 1 | 1 | 0 | 1 | 0 | 0 | 0 | 0 | 1 | 1 | 0 |
| TTC 05.0283 | 1 | 1 | 0 | 1 | 0 | 0 | 0 | 1 | 0 | 1 | 0 |
| TTC 05.0284 | 1 | 1 | 0 | 1 | 0 | 0 | 0 | 1 | 0 | 1 | 0 |
| TTC 05.0285 | 1 | 1 | 0 | 1 | 0 | 0 | 0 | 0 | 1 | 1 | 0 |
| TTC 05.0286 | 1 | 1 | 0 | 0 | 1 | 1 | 1 | 1 | 0 | 1 | 0 |
| TTC 05.0287 | 1 | 1 | 0 | 1 | 0 | 0 | 0 | 0 | 1 | 1 | 0 |
| TTC 05.0288 | 1 | 1 | 0 | 1 | 0 | 0 | 0 | 0 | 1 | 1 | 0 |
| TTC 05.0289 | 1 | 1 | 0 | 1 | 0 | 0 | 0 | 0 | 1 | 0 | 1 |
| TTC 05.0290 | 1 | 1 | 0 | 0 | 1 | 1 | 1 | 1 | 0 | 0 | 1 |
| TTC 05.0291 | 1 | 1 | 0 | 0 | 1 | 1 | 1 | 1 | 0 | 1 | 0 |
| TTC 05.0292 | 1 | 1 | 0 | 0 | 1 | 1 | 1 | 1 | 0 | 1 | 0 |
| TTC 05.0293 | 1 | 1 | 0 | 0 | 1 | 1 | 1 | 1 | 0 | 0 | 1 |

TABLE 1-continued

Presence or absence of incompatible marker pairs in a set of 144 *L. pneumophila* isolates

| Strain | Serotype | 019H4 | 011B3 | 005G5 | 009G2 | 008E11 | 030A9 | 009F12 | 035C6 | 007C10 | 012A12 |
|---|---|---|---|---|---|---|---|---|---|---|---|
| TTC 05.0294 | 1 | 1 | 0 | 0 | 1 | 1 | 1 | 1 | 0 | 1 | 0 |
| TTC 05.0295 | 1 | 1 | 0 | 0 | 1 | 1 | 1 | 1 | 0 | 0 | 1 |
| TTC 05.0352 | 1 | 1 | 0 | 0 | 1 | 1 | 1 | 1 | 0 | 0 | 1 |
| TTC 05.0353 | 1 | 1 | 0 | 1 | 0 | 0 | 0 | 0 | 1 | 0 | 1 |
| TTC 05.0354 | 1 | 1 | 0 | 0 | 1 | 1 | 1 | 1 | 0 | 0 | 1 |
| TTC 05.0355 | 1 | 1 | 0 | 1 | 0 | 0 | 0 | 0 | 1 | 1 | 0 |
| TTC 05.0356 | 1 | 1 | 0 | 0 | 1 | 1 | 1 | 1 | 0 | 0 | 1 |
| TTC 05.0358 | 1 | 1 | 0 | 0 | 1 | 1 | 1 | 0 | 1 | 0 | 1 |
| TTC 05.0359 | 1 | 1 | 0 | 0 | 1 | 1 | 1 | 1 | 0 | 1 | 0 |
| TTC 05.0360 | 1 | 1 | 0 | 0 | 1 | 1 | 1 | 1 | 0 | 0 | 1 |
| TTC 05.0361 | 1 | 1 | 0 | 0 | 1 | 1 | 1 | 0 | 1 | 0 | 1 |
| TTC 05.0362 | 1 | 1 | 0 | 0 | 1 | 1 | 1 | 1 | 0 | 1 | 0 |
| TTC 05.0363 | 1 | 1 | 0 | 0 | 1 | 1 | 1 | 1 | 0 | 0 | 1 |
| TTC 05.0364 | 1 | 1 | 0 | 1 | 0 | 0 | 0 | 0 | 1 | 0 | 1 |
| TTC 05.0365 | 1 | 1 | 0 | 1 | 0 | 0 | 0 | 0 | 1 | 1 | 0 |
| TTC 05.0366 | 1 | 1 | 0 | 0 | 1 | 1 | 1 | 1 | 0 | 1 | 0 |
| TTC 05.0367 | 1 | 1 | 0 | 0 | 1 | 1 | 1 | 1 | 0 | 0 | 1 |
| TTC 05.0368 | 6 | 0 | 1 | 1 | 0 | 0 | 0 | 0 | 1 | 0 | 1 |
| TTC 05.0369 | 1 | 1 | 0 | 0 | 1 | 1 | 1 | 0 | 1 | 0 | 1 |
| TTC 05.0370 | 1 | 1 | 0 | 1 | 0 | 0 | 0 | 0 | 1 | 1 | 0 |
| TTC 05.0371 | 7–>14 | 0 | 1 | 0 | 1 | 1 | 1 | 1 | 0 | 1 | 0 |

Sequence ID's:

SEQ ID NO 1: 11B3
GAATTCGTCGGAAACCAATCGGCGGTTTTTTTTAAGCCCTCACATG
AATCAACGGGTGGAGTCCAGCCTAAGTCTGAAATAATCTTTGAACT
ATCAATTTCCAGAGAACTCAGCAAGCGAGTATTTAAACTGCCCATT
CCTGTGATCTTGAACAGGCCGGCTAAAAAAGTAGTAGGGAAGTGAT
ACAATCTTAAATTGATTTTCATATTTTGGGCTAGTAAGGATAACAA
ATCCGCTAAAGACCAAGATTCATTATCTGCTACAAGATAAAGTTGA
TTTGCTGCTTTAGGATGTGTCATTACCATTAGAATAGCTGAAACCA
AGTTATCAATAAAAATAAAACTTCTCTTATTCTTTATACTGGCAAA
AGGCAATGGCCATCCTTTTTGTACCATACCCAATAATTTTAAAAAA
TTGGCTTTTACTCCAGGTCCATAAACAAGTGGAGGCCTCAAGATAA
CCACTTCCATGTCACTATTTTCACTAATCTCACGCAAATAGAGTTC
CGCTTCTAACTTACTCTGAGCATAAGAATCTTTTGGTTGGGCTGAA
TTTTTCTCAGAAAATGGGCTCTGAGGTAAGCTTACTTCTCCATTTA
CCTTAATAGTACTTAAAAATACAAATCGCTTTACTTTGTGTTTTGC
AGCTTGTTGAGCAAAATTCTTGGTGGCGATGCTGTTTATTTTGCAA
TACTCTTCCAGAGAGGAGGAGGTATCCTCTCTCATAACATGGACTC
GCGCAGCCAGATGTATGACAATATCGATTCCATTCAAAGCTTCTGA
CCCATCCGTTACTTGCTCCAGCTTATCAATTTCAACTTGCTCAACA
GACATGTATTGATTTTTTTGCCACACAGCACAACGAACCTCATACC
CTGCAGCAATAAGAACCGGGAACCAAGCTACTGCCCATAAAACCTG
GTGCGCCCGTCACTAATACTTTTGTCACTATATTACCTATGGCTT

SEQ ID NO 2: 5G5
TGACGAATCAGAGATTCGTCTTATTAACCTTTTTCTATGGAAAAAC
GCATGgTGGGACAAAGTATTCTGCTGAACATCACCTAAATGAATAT
AaaAAGAATCTGGAAGATGATATAAAGGCAATCGGTGTTCAAAGAA
AAATTTCACCAAATGCCTATGAAGATCTATTAAAAGAGAAAAAAGA
GCGCCTGGAACAAATCGAAAAATATATTGATTTAATCAAAGTACTC
AAAGAGAAATTTGATGAGCAAAGAGAAATAGACAAACTACGCACAG
AAGGAATCCCGCAATTACCTTCTGGAGTAAAGGAAGTCATTAAATC
TTCTGAAAATGCCTTTGCTTTAAGGCTTTCCCCGGATAGACCAGAC
TCATTTACCCGCTTTGATGATCCTCTGTTTAGTCTCAAAAGAAACA
GATCTCAATATGAAGCTGGGGGATACCAACGGGCAACTGATGGATT
AGGGGCTCGTTTGCGTTCTGAGCTTCTACCACCAGATAAAGACACT
CCTATTGTTTTTAATAAAAAATCACTGAAGGACAAAATCGTAGATT
CTGTTTTAGTGCAACTTGACAAAGATTTTAATACCAAAGATGGCGA
TCGTGGTCAAAAATTTGAGGATATAAAAAAACTCGTTCTAGAAGAG
TACAAGAAAATTGATTCCGACCTTCAGGTGGATGAGGATACCTATC
ACCAACCCCTTAACTTGGATTATTTGGAAAACATAGCATGTACGTT
AGATGAACACTCCCCTCGCAAAGAATGAGTTTATGGAATTATGGGT
GCCCCCAACCGAAGCTGATTATGGGCCCAAAAAAGGAAAGGGCAAC
GTGGAACTGAACAACTTAGTGGTATTTATTAACAACCCCAAGGAAT
ATAAAATTTGAATCTGAATACAAATACCATGGCCACTTACGGTCCA
ATATTCAATAACTGAAGATTATTTTTTATTGGCAAACCCCACCACC
TTCTCAAAGTCCAAATTTCGGTGAATTTTTTGCAATAAACACCCCC
CAGGC

-continued

SEQ ID NO 3: 9G2
CGCGAACCGAGAACCGTTCGGAGGCGATGAGAACGGAACCGATAAC
ACTCGTCCAAACAGCAGTTGAATTAAGATCATTCCCCTACGGAAAT
ACTCCACCACGGCGAAGCTAGGCATTCCCGCTGAGCAACAGCTCGA
CTCGATTATAAAAAACAACTCGGAAGAAGACATAAAAGCCATCAAT
AGCCAAAAAGGGATATCACGTTCATCGCTTATACCGATTCTCGTTA
AGGGAAAAAAAGGAACGACTTAAACAAATTCGAAAAATACATTCGA
GTTAATTCAACGTACTCAAAACAGAATATGATCACAACGGTGAAAT
AATGACTATAAAAAATAACATTATTCCACCTCTACCTTTCCGGATT
AAACCAAATAATCCAGTCTTCTGAGAATGCTGGTGCTGTAAGACTG
TCCCCAGATCGCCCTGATTTGGCAACCAGTTTTAAAAACCCTTTAT
TCAGGTTAAATAGACATTATGAAACCAGCGATTATAAACTGACAGA
AGGCTTAGGGGTTCGCCTCAGTTCAACGCTCTTGCCAGATCCTGAA
ACTCCTACGCCAATTAATAGAAAATCACAAAAAGAAAAAATTGTAG
AAACTGTTTTAGCTAAATTTCAACCAGAAAAAATAGCTGAACCAGA
CCGTGACCAAAAATTGAAAGAGCTAAAAGCCCTTTCTTCAGAAGAG
CTTGTAAAAATTGACTCCAATTTGTCAGTGGATATAAGCCATGATA
AACAAGAGACAAACTACGACTATCTGGAAAATATGATGGNCATGGA
TGAAGATAGTTTCATCAGGAATGGGGTTTGATCTATTCTCACAGCG
ACAGTAGATTCGAGCGCTTGGGGTTACTCAATCCCGCAGTCCTTTC
TATGATGGCGCCAAAGAATAAACAAAAAGACGATGCGGATAAAATG
TCCATCAAAGTACAATACCTAATAGCCGAGGCTAATTTTTATTGTA
AAACGAACAAATATTCCATGCTAACTTTCGGGAAATTTTTTTGACA
AGGAGCCTCATGCCACTGAAATTGCGAAAAGAGTCAAAGAAGGATT
GGTGCAAGGAGTAGATATAGAGCCTATCATATACAATTACATCAAC
AGCAACCATGCAGAGCTTGGATTAAAATCCCCTTTGACTGCCAAAC
AACAACAAGAAATCACCGATAAATTTTCGCAACATTACAATACCAT
TAAGGACTCCCCTCATTTTGATGAATTTTTTATCGCTGATCCTGAT
AAGAAGGGAAATATATTTACCCATCAGGGCAGACTCAGTTGCCATT
TCCTTGACTTCTTTGCCCGACAAACTAACGCCAAACATCTTTTGGG
AGAACTTGACGGTCACGCAGAAGCATTACTGGAAGGAACTTCAAAT
CGCTTAAATCATAAAAATGAAATTGTGGCGGAAGGATATGAGAAAA
TAGAGCAATTTAACAAGAAGTAGTAAGGCTTCTGGCTGAAAATAAC
CCAAAGAATGAACGATTCAGCTG

SEQ ID NO 4: 8 E11
GAATCGTCTCGATCTGGTAGCCTCAAGGATTCTGACATTGCCTCCT
TCGCCAGCGCGTCGCACGAATACAAGGGCTGCTCGTCATTAACCCC
AAACGGTGCCGTCGTGATCGTTATCACCCGGTCGCCATTCCTTACA
CCAACGACGGAGGATCGTGCTTTTCCAGTCGTTTTGCGTGAGCCAG
TCTTTGCGCAAAAAAACCAGATTTTCCAAGATTTGCTAACCGTAGT
GAAGCAACGAGATGATGAAAAGTTGCTGGAGCGAGTGTTTGTTCTG
GTTCGTTATGGTTGTATATATACCGGCACATTACGTGTAAATAACA
TTCCAGCTGGTCCATGGAAACATTTTTTCTATGTTCAAACAGTTAA
CATCGCAACAAGTGATATGAAGCCGCTGCTGGCAGCGCAAATTATT
GGCGGCTTACCTGTTTCCCAAAATGCTAAAGCGGACCTGGATATAG
CCTGTGGACCACTCACTTGGGAAGATGGTGAGTTTGATATTGAGTT
GATATAGAGTGTACTGCAGGGCTGATTCATATTGGCTAATAGCCAT
GGAATAATGTGAGTTGTATTGATAAGTAATACCTTAACTCTGTACG

-continued

GTACGATTTTTGGGACCGTCGTTGCGAGGAGCGTANCGACGAAGCA
ATCCAGTGGCCTGAATTCGTTGAAGTAGCTCACTGATTCATTGATA
ACCCATATTTTTTCCGCTAAGAAACGACATGGAGTCGTGAATGAGT
ATCACTGAGCTGGCAGATATTTTAAATGGTTATTTTTCATGGAACA
AGTCGCGAATCGAGTGTTTTGCGACGATGTTAATCTCTTTAATTCA
AGTAAGAAAGGTCAATTTAACTGAAATTGCATGTGGGTTTTCTAGC
CCTGCTAAAAAAGATTCAAGGTACACAAGAATCAAACCATTTTGAA
AAACCACGCATGACTCAACCGGATCGCATTGAAAAACTACTGGTGC
TATTGAACATTGCTTTTTGTTGGGCCCCTAAAAATGGAGAGTGGCG
GCATGTTCAGAAGACAATTAAAATCAAAAAACATGGTCGCAAAGGG
GTAAGTTTTTTTCGTTATGGACTTGATTTATTACATGATGCTGCGC
TTAATGGCTGTCAGTTTATTCACCATTCTTTCTCCGATATACTTGG
GTTTTTGTGCATTAGTCGCGTGATATGCGCTGCTGAATGAATTGGT
CCAATAACAAGGAAGAAGCATGCAAGTGAAACAACCAGCCATTTAC
ATCATGGCGAATAAACGCAATGGAACGATCTACACGGGTGTCACAA
GCGATTTGATCAAACGTGTCTATGAACATAAATATGGGGATGTACC
CGGGTTTACTCAAGAGCATGGATGTAAGTTTCTTGTTACTATGAGC
TCATGAAGACAGAACGAATCAAGCTGT

SEQ ID NO 5: 30A9
AGCTGATTCGTTTTTAGTTGTTTTTCTCGAGCTATGGCACTTATCA
TGTCTTCAATGAGCTCATAGTAAACAAGAAACTTACATCCATGCTC
TTGAGTAAACCCGGGTACATCCCCATATTTATGTTCAATAGACACG
TTTGATCAAATCGCTTGTGACACCCGTGTAGATTGTTCCATTGCGT
TTATTCGCCATGATGTAAATGGCTGGTTGTTTCACTTGCATGCTTC
TTCCTTGTTATTGGACCAATTCATTCAGCAGCGCATATCACGCGAC
TAATGCACAAAAACCCAAGTATATCGGAGAAAGAATGGTGAATAAA
CTGACAGCCATTAAGCGCAGCATCACGTAATAAATCAAGTCCATAA
CGAAAAAAACTTACCCCTTTGCGACCATGTTTTTTGATTTTAATTG
CCTTCTGAACATGCCGCCACTCTCCAGTTTTATGGGCCCAACAAAA
AGCAATGGTCAATAGCACCAGTAATTTTTCAATGCGATCGGTTGAG
TCATGTGTGTGTCTTCAAAATCGTTTGATTCTTGTGTACCTTGAAT
CTTGTTTAGCAGGGCTAGAAAAACCACATGCAATCTCAGTTAAATT
GACCGTTCTTACTTTGATTAAAGAGATTAACATCGTCGCAAAACAC
TCGATTCGCGACTTGTTCCATGAAAAATAACCATTTAAAATATCTG
CCAGATCAGTGATACTCATTCACGACTCCATGTCGTTTCTTAGCGG
AAAAAATATGGATTATCAATGAATCAGTGAGCTACTTCAACGAATT
CAGGCCACTGGAATGGCTTCGTCGCTACGCTCCTCGCAACGACGGT
CCCAAAAATCGTACCGTACAGAGCTACAAAACAGACAAGGATAATC
AGGAAGCCTTTTTATTTTGTCGCTTTGCTACCTCAAGAAATGTATA
CTGGCATTCTGTAACATTACCAACCATGTCATTTGTCATGACGGGG
TGTCGCTAAAACTTGAGACATGTAAAGTATTAAAATACTATAAGGC
GAAGAAGCAGATTAAATCGAAAGGGGAATTTCAGTAAACCGAATGC
CACCGAAAAGGATCCTAAATAAGGAAATAATAGAGATGGATCCCGT
GTACATGATAAACCACACCAGAGGCGAGCCTTTCTCGAAGAAAGAC
GAT

SEQ ID NO 6: 9F12
AATCAGCTGATTCGTTATGGGTTTATAGTCCATCTTGAATCATGTA
CAAACGAGAAATTGACCTTGAAAATAAGGCAATAAAAGTCCTGACT
GAGGAAGATAACAAAAGCTATGAAAAACAGGTCAAAGCGCAATTAG
ATAATATTAAAAATGTTTTAGAATCACTTGAAATGAAAATAATTAG
CCATTCTGAACAATGGGAGAAAATTAGAAATCCCGCAATTCAAAAA
GCGAAAGAATACTATTTAGGTGACATGGAAAAAGGTAACTGGGTAA
CTCAATGGGTAACGCAGTCCTGGATTAATGAGCTATCCTCTCTTCA
TTCCACCAGTGAATTTATTTATGAGTTAAATGCTTTACCCCCAAGA
AAAAGAGTACGTTTTATTGAAGGTGAAGAACAAAGTGTTGATACCA
CCTTGGAAAATTTAAGAAATCAAATTATTGATCGCTGTGGTTTGCG
AAGCATGATTGATGCGGAAGACAACTCTCCTGAACAACAATTATTG
AAAAAATCAATTGAATACTATGCCCACTCGCTGGCCATTTCAATGC
AGCGCTCCTTTTTAGTTAAGATTCCTGGAACTAATAATTATCAGGA
ATTTGACGGCATCAATGACAAAGGGGAGATAATAGAACGCAAAGAA
AACAATGGAACAGGCAAAGATTATTTGCAAAGTAATTTTACCCAAA
GAAAAATTAACGAGAAAATGAAGTTTTTCAGGGCAGTCAAAGCGTA
TCACCTCCATTTGATGTCCGAATTACCTGAAAATCCAGAACAATAT
AAAAACAGCTATATATTTATCAAAAATAACGATACTAAGGAGCTGT
ATTATATAAAACCTGATGGGAAATATGAAAAAGTAAAAATTATCAA
ATTCGATTTAATTGAAGAAAAAAATAGATAACAATAAAGATGCGAAT
AAATTAATCCTTCTCAGTAAGGAAGAAATTAAAGAAATTGTAACAT
TAAACGGAGGCCACTCCCCAGCAGAAGAGCACCATACTAAATTCAC
TGTTAACGATGTGGCTTTAAAACTAATGGGAGGCAAACCTGCCTAT
CCGTTTGCTCGAAAATGGTTTGGTCCTAAATTTGATGAAGCCTTGA
AACATCGAATGAACGTTGCTGCCAAATCCCTGCTCGTTGATGCAAT
AAATCATCCCAAAATTCACTTTGTATTTAACCGTTCACATGGAACG
AATTGAAGATTCTCTGCGAAGAAATTATTATAATTCTGACTTAATT
AAAAAGGTCGAGTTTAAACGAGTCTACGCGAGATGCGGGCGAATGA
ATACGCGCTTGTAAGAAGAACGAATTTGAAGCCCACACTTTTTTCC
ATAATCGATGCGGAAAAACAACTTACGGAACGTGGCGTTACTATTC
CAGAGTTTCCGATGAAGACTTTACGACGGTTC

SEQ ID NO 7: 35C6
CGAATCAGAGATTCGTCATGGGCATGCCCACCAGATGGACTTTATG
AAAGTTATGATTTCAAAATTTATTTTACCGACCCCCAACGAAAAGC
CTTCCTTATTCAAATCGACAATGAACTGGCCGGTTTTGCTTTATTA
AATAAATTCGGAATCCAAGCCGTTGATTGGAGTATAGGGGAGTTTT
TCATCCTGGCTAAATTCCAAGGGAAAGGCATTGGTCAATCAGTAGC
TCATCAACTATGGCGCACTCATCCAGGTGAATGGGAAATATCGGTC
ATTCCGGAAAACATACCGGCTTTATCGTTTTGGCGCCAGGCTGTAA
TGACCTATACTCTTGAACGGTACAAAGAACAGATAAAGACAGTGAA
TTATGATATCCACCAAACCCAACGCATTATTTTAAGTTTTAATACA
CAAAAACAGAACAAATCTTGTCATTCCATTCCAAAAAAACCTATTA
CAATAGATTTCGTGGATAATATCCCCAAATCTCTGGAAAAAAAGAT
GACAGAAGATCTGATAGCCTATGAAAGAACTCATGGTATTGATGTG
AACTACAAGCGTTTTTCGATAGTACTATCTGAAGGAGGGGTGACTT
GTGGCGTTATTAATGCCTTTACTGCTTTTGCGGAAATATACATCGA
TGACATATGGGTAGATAAAGCATATCGTGGTAAAGGATATGGCAGA
AAATTACTGCAAACTCTTGAGAATCATTTTAAAGGGCAAGGATTTA
ATAATATCAATTTATGTACCAGCGCCTTTCAAGCACCGGAATTTTA
CAGAAAATGCGGATATACGGCTGAATTTACACGAATCAATCAAGCC
AATCCCAAGCTTTCTAAAACCTTCTTTGTGAAATTTTTTGATGATG
AAAATCAAACACAAGGACTATTTTGAAAAACAGAACTTCTAAATAA
CCCCCACATCTTATTGATATTCAGAAGTTCTGAAAAAGTAATTTTC
AATTAAAGAGACTAATTAAAGTGCCTATAAACCGTCTTATTCCAAC
TGATTACATTAGTTTGTTTTAAGAGAAAAATCCTGGGAAGTCAGAA
ACCAACGTCGAATATTTTTTTCGGAGTATTTATGATACTGGCACCA
ATCTCTAATAATAGAGGAATCTATATCTTCCGGGATGTCATGTATG
CCTCGAGAAAAATTTCCCTGTAAAAGCAATAAACCTCCCAGATTAT
GCAAATAAAACTCAGGGTCTATAAAAATCATTGAAGTAGGATCATA
TAAGCAAAAATTAATAGGTTTTTATCGTATAATACATCCTGAGCG
TTGAAATTGGGGCCAAACTCATCATGAAGCCCTAAATTCCCCAGGA
TTTTGCCATCAAACCAGGCTCTGGGATATTTGCTCATGATATTTTT
ACCACCAGTTGCAGTTAAAATAATATCTGCTTTAGCCACTGCTTTT
TCAAGCTTATCGCGATCCTCGGGAGAATACGAATCAGCTGATT

SEQ ID NO 8: 7C10
AATCTTTATTAGAGAACTCTTCTGGGTCTTAAGGCATGAATCATGG
GGTTGTGGAGAGAACAATCCATTGAGGCATTTTAGGCTTATGGTAA
AAATGCAAATGCCTTAATGTATTCGGGTCAATTATATTATTGTTGA
TTTGCAAAACCCAGATAACACAAGATTGGGTAGAGTTCGCTGACAA
AGCCACAAAATTTGCCTGGCAGTTTGGTATTGGAAGCCTCTATGCC
CTCAGTGACTCGTTGTTAATCGATATCAATTATAATTTTATTTCAA
TTGGCGAAGTGAGGAATTCAGGTCAGTATAATGCTATTGCAGCCAA
TAATACTCCAGCTTCAGGTGCGCCAACAAAATTCACCAACGTGTAT
AGCAACCAGGCTGAAATTGGTATTCATTACCAATTTAATACTTAGC
GCCAATTCAAGGCAGGTTGAAGTAAAAAGATGACATCAATGGGAGC
CACTGTTTAACCTGCCCATTGCTATCTACTCGGCTGAAATGAAAAC
TACCTTCGTACTCAGGTCTTTCCTGGTTTTTAGCTGCCTGGTACTT
CACTCATAGTTTTCCTGGCAAATTTTCCCGTAATTTTACGGACTTT
ACCTCATGATGGAAAAAGTGGGCAGTCAATCTTCCATGATGTTAAA
CGAGCGGTGCTTTAAGTAGATTGTAATGTATATAAATCGTTGTCCT
TGATTGCGTTTCGCTACATCATAGCTATAAGGTTAATAAATATTCC
AAATAAATTGGGAAGTTGGCTTAAATGTGTCTATATTTGTTAGTAT
GTGAACACTTCCAGAATATCCAAACTCTACAGTAGGAATAAATTGA
ATTGATTTTAGAGTAAGAAAATGGATTGATAAACAGATTTGAATGT
TTCTTGTTAGCATCTCAATCAAGACAAACAAGGAAAGCATAATGTC
TAAGACTATATATTTTTTCAGTAACAATTTGAAACTGGAAGGAAAA
CTGGAAGAACCAACAGGTCAATGCCTTGGTTATGTTTTATTTGCTC
ATTGTTTTACCTGCGGAAAAGATATAGCTGCTGCAAGCAGAATTGC
CAGCGCTTTGGTTGCTAATGGATTTGCGGTGTTACGGTTTGATTTT
ACTGGCTTAGGTAGCAGCGAAGGTTCCTTTTCAGAAACGAATTTTT
CTTCAAATGTTGAAGATTTAGTTGCTGCCGCTGACTATTTAAGGAC
TCATTATCAAGCACCTGTTCTTTTGATAGGCCATAGTCTGACGATT
CTCTGATTCGT

SEQ ID NO 9: 12A12
AGGGTCAGATCTTGCTCTTCGCCTTTATCCATAAAAGACGGCAAGC
TTGGAATTAACGCTTGATAATTATTTCCCCAACGCATTCCATTATC
TTTCAAAAGGAATTAACTAAGTCCAGGAGCAGCGATTGGTAAGACT
TTTCGCGCATCGAGTTTTCTGGTGGGCTCTATCACATCAACAGTCG
AGGGAATAGAAAAGAAGCGATCTATTTATCAGATGCAGACAGAGAG
AATTTTTTATCTGTTTTGGGTGATGTTTGTTTAAAATATCAGTGGT
TATGCCATTCGTATTGTCTGATGACAAATCATTACCATTTACTTAT
TGAAACTCCGCTCGGTAACCTTTCAAAAGGAATGCGCTATCTGAAC
GGGGTATACACTCAGAAATTTAATAAATCACACAAGCGTATTGGGC
ACGTCCTGCAAGGTTGCTATAAATCTATATTGGTCACTACTCAAGA
ATTTGCAGAATTATAAGACAACATTATATGCAGGAGGCAAAGGACA
AGATCTGACCTACGCTCTAAACTATAATAATAGTTATAGATAATTG
ACTATTGGGATATTTTTACATGAATTACCTATTGCTGATTATCCTG
GGATTTGTAACTGCTCTTGGTTTTGCTGCGAATACACCTTGTTCTG
GAAAAAAGGGAGGTATTTCTCATTGTTTAGGTGAATATTTCGTATG
TAAAGATGGCTCANTAAGCCAATCAAAAAACAAATGCATTGATCTA

-continued

```
GATAAAAAAAAATGGTCAATAAATTTCACTCAATTTTGCTTTTTATT
TCCCTTCTTTTTAGTTGCACTGCCTATGCAAATACCATTAGCGGAT
TGGTTATAAAAATATCAGATGGTGATACATTAACTATCCTCACTAA
GGATAACGTTCAACTTAAAATTCGTTTATCAGAAATTGATGCACCA
GAGAAAAAACAACCATTTGGAAATAAATCCAAGCAGTCGCTCTCAA
ATCTTTGTTTTAATAAAGTAGCGATAGTTGATATTTTAAAAATTGA
TAGATATGGCCGCTCTGTTGGCAGAGTTAAATGTGATAATGTTGAT
GCTAATGAATACCAAGTAAAAAATGGGCTTGCATGGGTGTATGATA
AATATGTTACAGATCATTCGTTATATGCGCTTCAGGAACAAGCTAA
AAGCAAGGGAATAGGTTTGTGGTCGGAAAAATCCCCCATCCCTCCT
GGATTTCAGACAAATTAGCC
```

SEQ ID NO 10: 19H4

```
AAAGGAGACTTGGCAGCTCTCAAGAACTTGTTTGGTTGCAAGCAAA
AACTTCAACCCGGCTCTCTAATTAGCCTTGATAATACAACCTTTGC
CTTTCCTTGTAAGGGAGTTCCTACCCAATACTGGGATCTGGTAAAT
GGCTGGGAATTACAAAACAAGGTATCTATAGGTGAACCCATTAAAT
GGTCGGATATTAAGCAAAAAAATGATTGTTAAAAACCCTACTTGGA
ACTCTCTTACCCCTCCACTTCCTAAATTTGTTTCTTGTGATACAGG
CGAGACAAATTTCCTGAAAGAAAAATTAGGAGAAGATGGGAGGGTT
TTTATTGCTCAATTTGATCTAAAATCCACCTCTGCTTTTTTATTTC
AGCGTAAAAGTGATCAAAAAAAAATTTTTTATCAAGAAAGTATCCGC
TGAACATAAAAGACAGTATCAGCAGAGCGAACATTTGGCTCAATTT
ATCGCTTGCCCAGATTATATAGTTAATATTGCAATTAACTGCGTTT
CTAATGAAGAAGAAAACTCACTCTATTATATTTATCCCTATATTCA
TGGAAAACGCCTCTTTGCTGAACCAGAGGAAATAATAAGCCTTGCA
ACTGCATTAGCAAAATTACATCTTAAAAAAAAATCTTATCCTGATC
AACAATTGATTATTAAAAATACTACGGAACGAACATCACAGCTTAA
TTTTATAAGAAAGGCTTTAGCTAATGGATGTTATTCCTACATTCCA
TATTTCTCTTTTGTTAAAAAGATGGCTCAACAATATGATTTTGATT
GGATTAATCAAGAAGATGCCCAACCAATTCATGGTGATTTAAATGC
AGGAAATCTGTTACTATCCGAAAATAATATGATTTGCTTTTTTGAC
TTTGAAGACGCATTACATAGTTTCCATCCAGTAGTATTAGATTTGC
TATTCGTCATTGAGCGTATTATTTTTAATCAAAATAGTTCGACTGA
ACGGCTATTAAACCTTGGTCTCATGTTTATTCATGCATATAAAAAG
GCTGGTGGTACATACCGGTATAAAACGAGAGATGAATTTGGATTAA
CAATTCTTGCTTTAAAAGCATTTTGCTTGTTGACTTTGCTAGCAGA
GAAAAATAAAAATATACTGAACTCGGAATGGGATAAATTTTTTAAA
TTAACTCAGAAAGCAGAAAATGAACGGGATTTAATAAAAACAATTT
TACAAGGATAAGAAAGATAGTGTGAGAGTTCTTGTTACTGCACGGG
ATGTTGGTGCTGCATTAAACATTATTGAGATAGTAAAAATACTTAA
ACAATATACAGGTGTTACTGTATATATTTATGCTCAACCTCCCGCT
TCAAAATATTTTCTTCGGGCTGGGATTCAATCTGTATTTCAAGTTC
CACTACCACCAACCCGATCCTCAAATGAATCCAATCATCTACTATC
CTACGCCAATCAATTAATTGATAAATTAAATCCCGATATCATATTA
TCTGGATTATCATCTCCTGGCGAAGCTGGCATAGATGAAGCAATAA
TAGCTGTGTGTCCCGCGCATATCAAAACATTCATCCTTCAAGATTT
TTGGGGAGAAGTTAATTTTTTCTTTGAAAAATTAGCGGATTGCTAT
TTATGCATAGATCATCACGCTGCAGAAATTACAAAAAAACGATTTA
ATGCCAAAACCAGGGTGATAGGCTCCCCTCGCCATACCATTTTCAA
ACATAAAA
```

SEQ ID NO: 11 Protein sequence for marker 11B3 (SEQ ID NO: 1)

```
PVLIAAGYEVRCAVWQKNQYMSVEQVEIDKLEQVTDGSEALNGIDI
VIHLAARVHVMREDTSSSLEEYCKINSIATKNFAQQAAKHKVKRFV
FLSTIKVNGEVSLPQSPFSEKNSAQPKDSYAQSKLEAELYLREISE
NSDMEVVILRPPLVYGPGVKANFLKLLGMVQKGWPLPFASIKNKRS
FIFIDNLVSAILMVMTHPKAA
```

NQLYLVADNESWSLADLLSLLAQNMKIN-
LRLYHFPTTFLAGLFKITGMGSL NTR-
LLSSLEIDSSKIISDLGWTPPVDSCEGLKKTADWF

Sequence Comparison:

ref|YP_126160.1| hypothetical protein lpl0798 [*Legionella pneumophila* str. Lens} (SEQ ID NO: 11)

emb|CAH15032.1| hypothetical protein [*Legionella pneumophila* str. Lens] Length = 318 (SEQ ID NO: 12)

GENE ID: 3115428 lpl0798 | hypothetical protein [*Legionella pneumophila* str. Lens] (10 or fewer PubMed links)

Score = 338 bits (866), Expect (2) = 3e-93
Identities = 174/294 (59%), Positives = 221/294 (75%), Gaps = 0/294 (0%)
Frame = -1

```
QueryPVLIAAGYEVRCAVWQKNQYMSVEQVEIDKLEQVTDGSEALNGIDIVIHLAARVHVMRED
     P L++ G++VRCAV Q +   +  EQ+ I+ LE  TD ++AL  ++IVIHLAARVH+M+E
SbjctPALLSEGHDVRCAVLQLDSTLQAEQIVINNLEVHTDWTDALRNVEIVIHLAARVHIMKEY

QueryTSSSLEEYCKINSIATKNFAQQAAKHKVKRFVFLSTIKVNGEVSLPQSPFSEKNSAQPDK
      +S L+EYCKINSIATKNFA+QAA++ VKRF+FLSTIKV+GE S    PFSE    QP+D
SbjctVTSCLDEYCKINSIATKNFAEQAAQNNVKRFIFLSTIKVHGEFSQNSLPFSEDCRTQPED

QuerySYAQSKLEAELYLREISENSDMEVVILRPPLVYGPGVKANFLKLLGMVQKGWPLPFASIK
      YA+SKL AE Y++EI +N+ M+ VILRPPLVYGP VKANFLK+L +V K WPLPF SI
SbjctPYAKSKLFAEQYIQEICQNTRMDFVILRPPLVYGPYVKANFLKMLQLVDKKWPLPFGSIY

QueryNKRSFIFIDNLVSAILMVMTHPKAANQLYLVADNESWsladllsllAQNMKINLRLYHFP
     NKR+FI+IDNLVSAI  V+  P AANQ+YLVAD+ SWSL  L+  L++ M + L L   P
SbjctNKRTFIYIDNLVSAISAVVREPNAANQIYLVADDVSWSLTQLMQTLSRRMNVKLFLIPIP

QueryTIFLAGLFKITGMGSLNTRLLSSLEIDSSKIISDLGWTPPVDSCEGLKKTADWF
        L  LFK+ G+ ++NTRL SSLE+ + KI S LGWTPPV S EGL+KT  W+
SbjctVQILIFLFKLCGLKNINTRLFSSLEVSNKKIKSQLGWTPPVSSVEGLEKTVKWY
```

The invention claimed is:

1. A method for detecting the presence or absence of a serogroup of *Legionella pneumophila* in a sample, wherein said method comprises detecting the presence or absence of hybridization of nucleic acid of said sample to a specific genetic marker, said marker selected from the group consisting of:

a) SEQ ID NO: 1;

b) a fragment of SEQ ID NO: 1 comprising at least 50 contiguous nucleotides of SEQ ID NO: 1;

c) a homolog of SEQ ID NO: 1 at least 95% identical to SEQ ID NO: 1; and d) a fragment of said homolog comprising at least 50 contiguous nucleotides thereof wherein said fragment is at least 95% identical to SEQ ID NO: 1;

wherein the presence of hybridization indicates the presence in the sample of *Legionella pneumophila* of at least one of serogroups 2-14, and wherein the absence of hybridization indicates the absence in the sample of *Legionella pneumophila* of serogroups 2-14.

2. The method according to claim 1, which further comprises detecting the presence or absence of *Legionella pneumophila* serogroup 1A in said sample, wherein said method comprises detecting the presence or absence of hybridization of nucleic acid of said sample to a specific genetic marker, said marker selected from the group consisting of:

a) SEQ ID NO: 2;

b) a fragment of SEQ ID NO: 2 comprising at least 50 contiguous nucleotides of SEQ ID NO: 2;

c) a homolog of SEQ ID NO: 2 at least 95% identical to SEQ ID NO: 2; and d) a fragment of said homolog comprising at least 50 contiguous nucleotides thereof wherein said fragment is at least 95% identical to SEQ ID NO: 2;

wherein the presence of hybridization indicates the presence in the sample of *Legionella pneumophila* serogroup 1A, and wherein the absence of hybridization indicates the absence in the sample of *Legionella pneumophila* serogroup 1A.

3. The method according to claim 1, which further comprises detecting the presence or absence of *Legionella pneumophila* serogroup 1B in said sample, wherein said method comprises detecting the presence or absence of hybridization of nucleic acid of said sample to a specific genetic marker, said marker selected from the group consisting of:

a) any one of SEQ ID NOS: 3-5;

b) a fragment of any one of SEQ ID NOS: 3-5 comprising at least 50 contiguous nucleotides of one of SEQ ID NOS: 3-5;

c) a homolog of any one of SEQ ID NOS: 3-5 at least 95% identical to one of SEQ ID NOS: 3-5; and d) a fragment of said homolog comprising at least 50 contiguous nucleotides thereof wherein said fragment is at least 95% identical to one of SEQ ID NOS: 3-5;

wherein the presence of hybridization indicates the presence in the sample of *Legionella pneumophila* serogroup 1B, and wherein the absence of hybridization indicates the absence in the sample of *Legionella pneumophila* serogroup 1B.

4. The method according to claim 1, wherein said nucleic acid of said sample is genomic DNA.

5. The method of claim 4 wherein said genomic DNA is fragmented.

6. The method of claim 1, wherein said fragment of b) comprises at least 100 contiguous nucleotides of SEQ ID NO: 1, or wherein said fragment of d) comprises at least 100 contiguous nucleotides of said homolog.

7. A hybridization assay kit comprising an array having attached thereto a marker consisting of SEQ ID NO: 1 or a homolog of SEQ ID NO: 1 at least 95% identical thereto.

* * * * *